US 11,596,550 B2

(12) United States Patent
Chang et al.

(10) Patent No.: US 11,596,550 B2
(45) Date of Patent: Mar. 7, 2023

(54) ADJUSTABLE GLAUCOMA TREATMENT DEVICES AND ASSOCIATED SYSTEMS AND METHODS

(71) Applicant: Shifamed Holdings, LLC, Campbell, CA (US)

(72) Inventors: Robert Chang, Belmont, CA (US); Tom Saul, Moss Beach, CA (US); Claudio Argento, Felton, CA (US); Eric Schultz, Los Altos, CA (US); Katherine Sapozhnikov, Campbell, CA (US); Richard Lilly, San Jose, CA (US); Michael Drews, Palo Alto, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 17/622,672

(22) PCT Filed: Apr. 16, 2021

(86) PCT No.: PCT/US2021/027742
§ 371 (c)(1),
(2) Date: Dec. 23, 2021

(87) PCT Pub. No.: WO2021/212007
PCT Pub. Date: Oct. 21, 2021

(65) Prior Publication Data
US 2022/0202613 A1 Jun. 30, 2022

Related U.S. Application Data

(60) Provisional application No. 63/039,237, filed on Jun. 15, 2020, provisional application No. 63/010,854, filed on Apr. 16, 2020.

(51) Int. Cl.
*A61F 9/007* (2006.01)
(52) U.S. Cl.
CPC .... *A61F 9/00781* (2013.01); *A61F 2250/001* (2013.01); *A61F 2250/0013* (2013.01)
(58) Field of Classification Search
CPC ........ A61F 9/00; A61F 9/007; A61F 9/00781; A61F 9/0017; A61F 2210/0014; A61M 27/002
See application file for complete search history.

(56) References Cited

U.S. PATENT DOCUMENTS

| 4,401,107 A | 8/1983 | Harber et al. |
| 4,595,390 A | 6/1986 | Hakim et al. |

(Continued)

FOREIGN PATENT DOCUMENTS

| AU | 2014201621 B2 | 3/2016 |
| AU | 2016201445 B2 | 3/2016 |

(Continued)

OTHER PUBLICATIONS

International Search Report and Written Opinion received for PCT Application No. PCT/US22/13336, filed on Jan. 21, 2022, Applicant: Shifamed Holdings, LLC, dated Apr. 11, 2022, 9 pages.

(Continued)

*Primary Examiner* — Vi X Nguyen
(74) *Attorney, Agent, or Firm* — Perkins Cole LLP

(57) ABSTRACT

The present technology is directed to implantable medical devices for draining fluid from a first body region to a second body region. Some embodiments of the present technology provide adjustable devices that are selectively titratable to provide various levels of therapy. For example, the adjustable devices can have a drainage element with a lumen extending therethrough, a flow control element, and an actuation assembly. The actuation assembly can drive (Continued)

movement of the flow control element to change a dimension of and/or a flow resistance through the lumen, thereby increasing or decreasing the relative drainage rate of aqueous from an eye. In some embodiments, the actuation assembly and the flow control element together operate as a ratchet mechanism that can selectively move the flow control element between a plurality of positions and lock the device in a desired configuration until further actuation of the actuation assembly.

18 Claims, 10 Drawing Sheets

(56) References Cited

U.S. PATENT DOCUMENTS

| | | |
|---|---|---|
| 5,070,697 A | 12/1991 | Van Zeggeren |
| 5,123,906 A | 6/1992 | Kelman |
| 5,300,020 A | 4/1994 | L'Esperance, Jr. |
| 5,476,445 A | 12/1995 | Baerveldt et al. |
| 5,601,094 A | 2/1997 | Reiss |
| 6,077,299 A | 6/2000 | Adelberg et al. |
| 6,203,513 B1 | 3/2001 | Yaron et al. |
| 6,261,256 B1 | 7/2001 | Ahmed |
| 6,450,984 B1 | 9/2002 | Lynch et al. |
| 6,508,779 B1 | 1/2003 | Suson |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,736,791 B1 | 5/2004 | Tu et al. |
| 6,789,447 B1 | 9/2004 | Zinck |
| 7,025,740 B2 | 4/2006 | Ahmed |
| 7,207,965 B2 | 4/2007 | Simon |
| 7,354,416 B2 | 4/2008 | Quiroz-Mereado et al. |
| 7,364,564 B2 | 4/2008 | Sniegowski et al. |
| 7,458,953 B2 | 12/2008 | Peyman |
| 7,699,882 B2 | 4/2010 | Stamper et al. |
| 7,717,872 B2 | 5/2010 | Shetty |
| 7,947,008 B2 | 5/2011 | Grahn et al. |
| 8,012,134 B2 | 9/2011 | Claude et al. |
| 8,206,333 B2 | 6/2012 | Schmidt et al. |
| 8,206,440 B2 | 6/2012 | Guarnieri |
| 8,298,240 B2 | 10/2012 | Giger et al. |
| 8,308,701 B2 | 11/2012 | Horvath et al. |
| 8,506,515 B2 | 8/2013 | Burns et al. |
| 8,540,659 B2 | 9/2013 | Berlin |
| 8,579,848 B2 | 11/2013 | Field et al. |
| 8,585,629 B2 | 11/2013 | Grabner et al. |
| 8,663,303 B2 | 3/2014 | Horvath et al. |
| 8,702,639 B2 | 4/2014 | Van Der Mooren et al. |
| 8,721,702 B2 | 5/2014 | Romoda et al. |
| 8,753,305 B2 | 6/2014 | Field et al. |
| 8,758,290 B2 | 6/2014 | Horvath et al. |
| 8,765,210 B2 | 7/2014 | Romoda et al. |
| 8,771,220 B2 | 7/2014 | Nissan et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,882,781 B2 | 11/2014 | Smedley et al. |
| 8,915,877 B2 | 12/2014 | Cunningham et al. |
| 8,974,511 B2 | 3/2015 | Horvath et al. |
| 9,017,276 B2 | 4/2015 | Horvath et al. |
| 9,095,411 B2 | 8/2015 | Horvath et al. |
| 9,095,413 B2 | 8/2015 | Romoda et al. |
| 9,113,994 B2 | 8/2015 | Horvath et al. |
| 9,125,723 B2 | 9/2015 | Horvath et al. |
| 9,192,516 B2 | 11/2015 | Horvath et al. |
| 9,226,851 B2 | 1/2016 | Gunn |
| 9,271,869 B2 | 3/2016 | Horvath et al. |
| 9,283,115 B2 | 3/2016 | Lind et al. |
| 9,283,116 B2 | 3/2016 | Romoda et al. |
| 9,289,324 B2 | 3/2016 | Johnson et al. |
| 9,326,891 B2 | 5/2016 | Horvath et al. |
| 9,375,347 B2 | 6/2016 | Stergiopulos |
| 9,393,153 B2 | 7/2016 | Horvath et al. |
| 9,555,410 B2 | 1/2017 | Brammer et al. |
| 9,585,789 B2 | 3/2017 | Silvestrini et al. |
| 9,585,790 B2 | 3/2017 | Horvath et al. |
| 9,592,154 B2 | 3/2017 | Romoda et al. |
| 9,610,195 B2 | 4/2017 | Horvath |
| 9,636,254 B2 | 5/2017 | Yu et al. |
| 9,655,778 B2 | 5/2017 | Tyler |
| 9,655,779 B2 | 5/2017 | Bigler et al. |
| 9,693,900 B2 | 7/2017 | Gallardo Inzunza |
| 9,693,901 B2 | 7/2017 | Horvath et al. |
| 9,757,276 B2 | 9/2017 | Penhasi |
| 9,808,373 B2 | 11/2017 | Horvath et al. |
| 9,877,866 B2 | 1/2018 | Horvath et al. |
| 9,883,969 B2 | 2/2018 | Horvath et al. |
| 9,980,854 B2 | 5/2018 | Horvath et al. |
| 10,004,638 B2 | 6/2018 | Romoda et al. |
| 10,080,682 B2 | 9/2018 | Horvath et al. |
| 10,085,884 B2 | 10/2018 | Reitsamer et al. |
| 10,154,924 B2 | 12/2018 | Clauson et al. |
| 10,159,600 B2 | 12/2018 | Horvath et al. |
| 10,195,078 B2 | 2/2019 | Horvath et al. |
| 10,195,079 B2 | 2/2019 | Horvath et al. |
| 10,231,871 B2 | 3/2019 | Hill |
| 10,238,536 B2 | 3/2019 | Olson et al. |
| 10,285,853 B2 | 5/2019 | Rangel-Friedman et al. |
| 10,307,293 B2 | 6/2019 | Horvath et al. |
| 10,314,743 B2 | 6/2019 | Romoda et al. |
| 10,322,267 B2 | 6/2019 | Hakim |
| 10,369,048 B2 | 8/2019 | Horvath et al. |
| 10,405,903 B1 | 9/2019 | Biesinger et al. |
| 10,335,030 B2 | 10/2019 | Alhourani |
| 10,342,703 B2 | 11/2019 | Siewert |
| 10,463,537 B2 | 11/2019 | Horvath et al. |
| 10,470,927 B2 | 11/2019 | Horvath et al. |
| 10,363,168 B2 | 12/2019 | Schieber et al. |
| 10,492,948 B2 | 12/2019 | Baerveldt |
| 10,524,959 B2 | 1/2020 | Horvath |
| 10,524,958 B2 | 3/2020 | Camras et al. |
| 10,596,035 B2 | 4/2020 | Stergiopulos et al. |
| 10,758,412 B2 | 4/2020 | Velasquez |
| 11,122,975 B2 | 1/2021 | Rodger et al. |
| 10,912,675 B2 | 2/2021 | Lubatschowski |
| 11,166,847 B2 | 2/2021 | Badawi et al. |
| 10,952,897 B1 | 3/2021 | Smith |
| 10,960,074 B2 | 3/2021 | Berdahl |
| 11,039,954 B2 | 6/2021 | Cohen et al. |
| 11,058,581 B2 * | 7/2021 | Mixter ............... A61F 9/0017 |
| 11,065,154 B1 | 7/2021 | Sponsel et al. |
| 11,083,624 B2 | 8/2021 | Stein et al. |
| 11,166,848 B2 | 11/2021 | Mixter et al. |
| 11,166,849 B2 | 11/2021 | Mixter et al. |
| 11,291,585 B2 | 4/2022 | Schultz et al. |
| 11,517,477 B2 | 12/2022 | Lilly et al. |
| 11,529,258 B2 | 12/2022 | Chang et al. |
| 2001/0011585 A1 | 8/2001 | Cassidy et al. |
| 2002/0177891 A1 | 11/2002 | Miles et al. |
| 2002/0193725 A1 | 12/2002 | Odrich |
| 2003/0127090 A1 | 7/2003 | Gifford et al. |
| 2003/0163079 A1 | 8/2003 | Burnett |
| 2004/0010219 A1 | 1/2004 | McCusker et al. |
| 2004/0254520 A1 | 12/2004 | Porteous et al. |
| 2005/0049578 A1 | 3/2005 | Tu et al. |
| 2006/0155300 A1 | 7/2006 | Stamper et al. |
| 2007/0010837 A1 | 1/2007 | Tanaka |
| 2007/0078371 A1 | 4/2007 | Brown et al. |
| 2007/0088432 A1 | 4/2007 | Solovay et al. |
| 2008/0077071 A1 | 3/2008 | Yaron et al. |
| 2008/0119891 A1 | 5/2008 | Miles et al. |
| 2008/0125691 A1 | 5/2008 | Yaron et al. |
| 2008/0228127 A1 | 9/2008 | Burns et al. |
| 2009/0036818 A1 | 2/2009 | Grahn et al. |
| 2009/0243956 A1 | 10/2009 | Keilman et al. |
| 2009/0314970 A1 | 12/2009 | McAvoy et al. |
| 2009/0326517 A1 | 12/2009 | Bork et al. |
| 2010/0114006 A1 | 5/2010 | Baerveldt |
| 2010/0234791 A1 | 9/2010 | Lynch et al. |

(56) References Cited

U.S. PATENT DOCUMENTS

| | | |
|---|---|---|
| 2010/0241077 A1 | 9/2010 | Geipel et al. |
| 2010/0249691 A1 | 9/2010 | Van Der Mooren et al. |
| 2011/0105986 A1 | 5/2011 | Bronstein et al. |
| 2012/0065570 A1 | 3/2012 | Yeung et al. |
| 2012/0089073 A1 | 4/2012 | Cunningham, Jr. |
| 2012/0232461 A1 | 9/2012 | Seaver et al. |
| 2013/0085440 A1 | 4/2013 | Bohm et al. |
| 2013/0131577 A1 | 5/2013 | Bronstein et al. |
| 2013/0150773 A1 | 6/2013 | Nissan et al. |
| 2013/0150776 A1 | 6/2013 | Bohm et al. |
| 2013/0158381 A1 | 6/2013 | Rickard |
| 2013/0197621 A1 | 8/2013 | Ryan et al. |
| 2013/0199646 A1 | 8/2013 | Brammer et al. |
| 2013/0205923 A1 | 8/2013 | Brammer et al. |
| 2013/0211312 A1 | 8/2013 | Gelvin |
| 2013/0267887 A1 | 10/2013 | Kahook et al. |
| 2013/0317412 A1 | 11/2013 | Dacquay et al. |
| 2013/0338564 A1 | 12/2013 | Rickard et al. |
| 2014/0046439 A1 | 2/2014 | Dos Santos et al. |
| 2014/0081195 A1 | 3/2014 | Clauson et al. |
| 2014/0309611 A1 | 10/2014 | Wilt et al. |
| 2015/0011926 A1 | 1/2015 | Reitsamer et al. |
| 2015/0034217 A1 | 2/2015 | Vad |
| 2015/0045716 A1 | 2/2015 | Gallardo Inzunza |
| 2015/0142049 A1 | 5/2015 | Delgado et al. |
| 2015/0230843 A1 | 8/2015 | Palmer et al. |
| 2015/0313603 A1 | 11/2015 | Bodewadt et al. |
| 2016/0151179 A1 | 6/2016 | Favier et al. |
| 2016/0220794 A1 | 8/2016 | Negre |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0287439 A1 | 10/2016 | Stergiopulos |
| 2016/0354244 A1 | 12/2016 | Horvath et al. |
| 2016/0354245 A1 | 12/2016 | Horvath et al. |
| 2017/0027582 A1 | 2/2017 | Khoury et al. |
| 2017/0071791 A1* | 3/2017 | Piven ............... A61F 9/00781 |
| 2017/0087016 A1 | 3/2017 | Camras |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0312125 A1 | 11/2017 | Clauson et al. |
| 2017/0348149 A1 | 12/2017 | Stergiopulos et al. |
| 2017/0348150 A1 | 12/2017 | Horvath et al. |
| 2018/0014828 A1 | 1/2018 | Fonte et al. |
| 2018/0028361 A1 | 2/2018 | Haffner et al. |
| 2018/0092775 A1 | 4/2018 | de Juan, Jr et al. |
| 2018/0147089 A1 | 5/2018 | Horvath et al. |
| 2018/0206878 A1 | 7/2018 | Uspenski et al. |
| 2018/0250166 A1 | 9/2018 | Lubatschowski |
| 2019/0000673 A1 | 1/2019 | Fjield et al. |
| 2019/0021907 A1 | 1/2019 | Horvath et al. |
| 2019/0038462 A1 | 2/2019 | Vandiest et al. |
| 2019/0046356 A1 | 2/2019 | Laroche |
| 2019/0060118 A1 | 2/2019 | Hill |
| 2019/0133826 A1 | 3/2019 | Horvath et al. |
| 2019/0121278 A1 | 4/2019 | Kawamura et al. |
| 2019/0142632 A1 | 5/2019 | Badawi et al. |
| 2019/0167475 A1 | 6/2019 | Horvath et al. |
| 2019/0240069 A1 | 8/2019 | Horvath et al. |
| 2019/0247231 A1 | 8/2019 | McClunan |
| 2019/0274881 A1 | 9/2019 | Romoda et al. |
| 2019/0274882 A1 | 9/2019 | Romoda et al. |
| 2019/0307608 A1 | 10/2019 | Lee et al. |
| 2019/0344057 A1 | 11/2019 | Cima et al. |
| 2019/0350758 A1 | 11/2019 | Horvath et al. |
| 2019/0353269 A1 | 11/2019 | Ossmer et al. |
| 2019/0358086 A1 | 11/2019 | Camras et al. |
| 2019/0374384 A1 | 12/2019 | Xie et al. |
| 2020/0069469 A1 | 3/2020 | Horvath et al. |
| 2020/0085620 A1 | 3/2020 | Euteneuer et al. |
| 2020/0121503 A1 | 4/2020 | Badawi et al. |
| 2020/0121504 A1 | 4/2020 | Stegmann et al. |
| 2020/0129332 A1 | 4/2020 | Van Der Mooren et al. |
| 2020/0170839 A1 | 6/2020 | Borrmann et al. |
| 2020/0179171 A1 | 6/2020 | Crimaldi et al. |
| 2020/0214891 A1 | 7/2020 | Bigler et al. |
| 2020/0229977 A1 | 7/2020 | Mixter et al. |
| 2020/0229980 A1 | 7/2020 | Horvath |
| 2020/0229981 A1 | 7/2020 | Mixter et al. |
| 2020/0229982 A1 | 7/2020 | Mixter et al. |
| 2020/0246188 A1 | 8/2020 | Horvath et al. |
| 2020/0261271 A1 | 8/2020 | Horvath et al. |
| 2020/0276050 A1 | 9/2020 | Simons et al. |
| 2020/0306086 A1 | 10/2020 | Da Silva Curiel et al. |
| 2020/0345549 A1 | 11/2020 | Lu et al. |
| 2021/0015665 A1 | 1/2021 | Hacker et al. |
| 2021/0030590 A1 | 2/2021 | Blanda et al. |
| 2021/0038158 A1 | 2/2021 | Haffner et al. |
| 2021/0069486 A1 | 3/2021 | Hakim |
| 2021/0106462 A1 | 4/2021 | Sherwood et al. |
| 2021/0137736 A1 | 5/2021 | Cavuto et al. |
| 2021/0161713 A1 | 6/2021 | Bouremel et al. |
| 2021/0196516 A1 | 7/2021 | Ianchulev |
| 2021/0205132 A1 | 7/2021 | Horvath et al. |
| 2021/0212858 A1 | 7/2021 | Tran et al. |
| 2021/0251806 A1 | 8/2021 | Schultz et al. |
| 2021/0298948 A1 | 9/2021 | Haffner et al. |
| 2021/0315806 A1 | 10/2021 | Haffner |
| 2021/0330499 A1 | 10/2021 | Wardle et al. |
| 2022/0087865 A1 | 3/2022 | Argento et al. |
| 2022/0142818 A1 | 5/2022 | Chang et al. |
| 2022/0160545 A1 | 5/2022 | Mixter et al. |
| 2022/0160546 A1 | 5/2022 | Mixter et al. |
| 2022/0249155 A1 | 8/2022 | Lilly et al. |
| 2022/0249285 A1 | 8/2022 | Chang et al. |
| 2022/0339035 A1 | 10/2022 | Lilly et al. |
| 2022/0387216 A1 | 12/2022 | Schultz et al. |
| 2022/0387217 A1 | 12/2022 | Argento et al. |

FOREIGN PATENT DOCUMENTS

| | | |
|---|---|---|
| AU | 2018200325 A1 | 2/2018 |
| AU | 2017274654 | 12/2018 |
| AU | 2020201818 | 4/2020 |
| AU | 2017439185 | 5/2020 |
| AU | 2018412569 | 10/2020 |
| BR | 112017025859 A2 | 8/2018 |
| BR | 112020008969 | 10/2020 |
| CA | 2987953 A1 | 12/2016 |
| CA | 3080713 | 5/2019 |
| CA | 3093160 | 9/2019 |
| CN | 104490515 | 4/2015 |
| CN | 106726124 | 5/2017 |
| CN | 108743016 A | 11/2018 |
| CN | 111405875 | 7/2020 |
| CO | 2020011460 | 11/2020 |
| DE | 10217061 | 3/2003 |
| DE | 102010015447 A1 | 10/2011 |
| DE | 102017124885 A1 | 4/2019 |
| DE | 102018112065 A1 | 11/2019 |
| DE | 102019204846 A1 | 10/2020 |
| EP | 1292256 A1 | 3/2003 |
| EP | 1737531 A2 | 1/2007 |
| EP | 3302381 A1 | 4/2018 |
| EP | 1765234 | 10/2019 |
| EP | 2999430 | 11/2019 |
| EP | 2677981 | 4/2020 |
| EP | 3659495 | 6/2020 |
| EP | 3518846 | 8/2020 |
| EP | 3666236 | 8/2020 |
| EP | 3687374 | 8/2020 |
| EP | 3706653 | 9/2020 |
| EP | 3730104 | 10/2020 |
| EP | 3735947 | 11/2020 |
| EP | 3773377 | 2/2021 |
| EP | 3846747 | 7/2021 |
| EP | 3846748 | 7/2021 |
| EP | 3329884 | 8/2021 |
| EP | 2389138 | 9/2021 |
| EP | 3870120 | 9/2021 |
| EP | 3313335 | 11/2021 |
| ES | 2725550 | 9/2019 |

(56) References Cited

FOREIGN PATENT DOCUMENTS

| | | |
|---|---|---|
| HK | 1252748 | 5/2019 |
| HU | E043303 | 8/2019 |
| JP | 5576427 B2 | 8/2014 |
| JP | 2018519892 | 7/2018 |
| JP | 2018130580 | 8/2018 |
| JP | 2019517366 | 6/2019 |
| JP | 2019205934 | 12/2019 |
| JP | 2020049361 | 4/2020 |
| KR | 2018015684 A | 2/2018 |
| KR | 20190019966 | 2/2019 |
| KR | 20200021551 | 2/2020 |
| KR | 20200059305 | 5/2020 |
| PL | 2640455 | 8/2019 |
| PT | 2640455 | 5/2019 |
| RU | 2687764 | 5/2019 |
| RU | 2018142990 | 6/2020 |
| SG | 11202008604 | 10/2020 |
| TR | 201906873 | 6/2019 |
| WO | WO1992019294 | 11/1992 |
| WO | WO2004081613 | 9/2004 |
| WO | WO2007011302 A1 | 1/2007 |
| WO | WO2010111528 | 9/2010 |
| WO | WO2014130574 | 8/2014 |
| WO | WO2016100500 | 6/2016 |
| WO | WO2016149425 | 9/2016 |
| WO | WO2016196841 A1 | 12/2016 |
| WO | WO2018229766 | 12/2018 |
| WO | WO2019018807 | 1/2019 |
| WO | WO2019094004 A1 | 5/2019 |
| WO | WO2019165053 | 8/2019 |
| WO | WO2019172940 | 9/2019 |
| WO | WO2020150663 | 7/2020 |
| WO | WO2020215068 | 10/2020 |
| WO | WO2020223491 | 11/2020 |
| WO | WO2020231993 | 11/2020 |
| WO | WO2020247365 | 12/2020 |
| WO | WO2020261184 | 12/2020 |
| WO | WO2021007294 | 1/2021 |
| WO | WO2021007296 | 1/2021 |
| WO | WO2021028703 | 2/2021 |
| WO | WO2021068078 | 4/2021 |
| WO | WO2021072315 | 4/2021 |
| WO | WO2021072317 | 4/2021 |
| WO | WO2021113730 | 6/2021 |
| WO | WO2021142255 | 7/2021 |
| WO | WO2021151007 | 7/2021 |
| WO | WO2021163566 | 8/2021 |
| WO | WO2021168130 | 8/2021 |
| WO | WO2021174298 | 9/2021 |
| WO | WO2021176332 | 9/2021 |
| WO | WO2021188952 | 9/2021 |
| WO | WO2021204312 | 10/2021 |
| WO | WO2021212007 | 10/2021 |
| WO | WO2022220861 | 10/2022 |
| ZA | 201708295 | 5/2020 |

OTHER PUBLICATIONS

International Search Report and Written Opinion received for PCT Application No. PCT/US21/49140, filed on Sep. 3, 2021, Applicant: Shifamed Holdings, LLC, dated Dec. 7, 2021, 22 pages.

International Search Report and Written Opinion received for PCT Application No. PCT/US18/43158, filed on Jul. 20, 2018, Applicant: Shifamed Holdings, LLC, dated Nov. 23, 2018, 12 pages.

International Search Report and Written Opinion received for PCT Application No. PCT/US20/41152, filed on Jul. 8, 2020, Applicant: Shifamed Holdings, LLC, dated Oct. 28, 2020, 13 pages.

International Search Report and Written Opinion received for PCT Application No. PCT/US20/14186, filed on Jan. 17, 2020, Applicant: Shifamed Holdings, LLC, dated Jun. 4, 2020, 13 pages.

International Search Report and Written Opinion received for PCT Application No. PCT/US20/55144, filed on Oct. 9, 2020, Applicant: Shifamed Holdings, LLC, dated Feb. 1, 2021, 16 pages.

International Search Report and Written Opinion received for PCT Application No. PCT/US20/55141, filed on Oct. 9, 2020, Applicant: Shifamed Holdings, LLC, dated Jan. 29, 2021, 11 pages.

International Search Report and Written Opinion received for PCT Application No. PCT/US21/14774, filed on Jan. 22, 2021, Applicant: Shifamed Holdings, LLC, dated May 12, 2021, 10 pages.

International Search Report and Written Opinion received for PCT Application No. PCT/US21/17962, filed on Feb. 12, 2021, Applicant: Shifamed Holdings, LLC, dated Jun. 7, 2021, 12 pages.

International Search Report and Written Opinion received for PCT Application No. PCT/US21/23238, filed on Mar. 19, 2021, Applicant: Shifamed Holdings, LLC, dated Jul. 8, 2021, 10 pages.

International Search Report and Written Opinion received for PCT Application No. PCT/US21/18601, filed on Feb. 18, 2021, Applicant: Shifamed Holdings, LLC, dated Jul. 19, 2021, 12 pages.

International Search Report and Written Opinion received for PCT Application No. PCT/US21/55258, filed on Oct. 15, 2021, Applicant: Shifamed Holdings, LLC, dated Feb. 28, 18 pages.

International Search Report and Written Opinion received for International PCT Application No. PCT/US2021/027742, filed on Apr. 16, 2021; Applicant: Shifamed Holdings, LLC; dated Oct. 7, 2021, 13 pages.

International Search Report and Written Opinion received for PCT Application No. PCT/US22/35324, filed on Jun. 28, 2022, Applicant: Shifamed Holdings, LLC, dated Nov. 22, 2022, 12 pages.

* cited by examiner

DETAIL A

ADJUSTABLE GLAUCOMA TREATMENT DEVICES AND ASSOCIATED SYSTEMS AND METHODS

CROSS-REFERENCE TO RELATED APPLICATION(S)

This application is a 35 U.S.C. § 371 U.S. National Phase application of International Patent Application No. PCT/US2021/027742, filed Apr. 16, 2021, which claims priority to the following pending applications:

U.S. Provisional Patent Application No. 63/010,854, filed Apr. 16, 2020; and

U.S. Provisional Patent Application No. 63/039,237, filed Jun. 15, 2020.

All of the foregoing applications are incorporated herein by reference in their entireties. Further, components and features of embodiments disclosed in the applications incorporated by reference may be combined with various components and features disclosed and claimed in the present application.

TECHNICAL FIELD

The present technology generally relates to implantable medical devices and, in particular, to intraocular systems, devices, and associated methods for selectively controlling fluid flow between different portions of a patient's eye.

BACKGROUND

Glaucoma is a degenerative ocular condition involving damage to the optic nerve that can cause progressive and irreversible vision loss. Glaucoma is frequently associated with ocular hypertension, an increase in pressure within the eye, and may result from an increase in production of aqueous humor ("aqueous") within the eye and/or a decrease in the rate of outflow of aqueous from within the eye into the blood stream. Aqueous is produced in the ciliary body at the boundary of the posterior and anterior chambers of the eye. It flows into the anterior chamber and eventually into the capillary bed in the sclera of the eye. Glaucoma is typically caused by a failure in mechanisms that transport aqueous out of the eye and into the blood stream.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

Figure 1A:
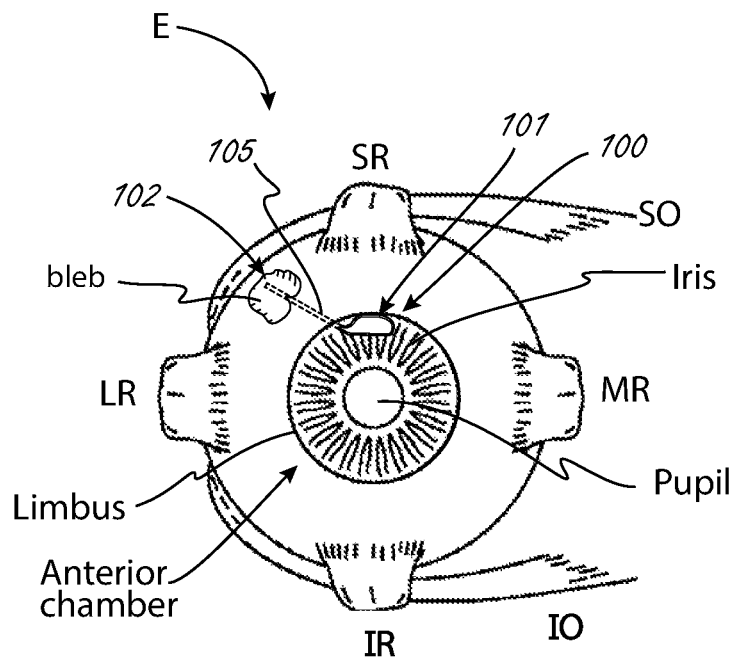
FIG. 1A is a simplified front view of an eye with an implanted shunt configured in accordance with an embodiment of the present technology.

The present technology is directed to implantable systems and devices for facilitating the flow of fluid between a first body region and a second body region. In embodiments, the devices are selectively adjustable to control the amount of fluid flowing between the first body region and the second body region. The devices generally include a drainage and/or shunting element having a lumen extending therethrough for draining or otherwise shunting fluid between the first and second body regions. Some embodiments include an actuation assembly that can drive movement of a flow control element to change the flow resistance through the lumen, thereby increasing or decreasing the relative drainage rate of fluid between the first body region and the second body region.

In particular, some embodiments of the present technology provide adjustable devices that are selectively titratable to provide various levels of therapy. For example, the devices can be adjusted through a number of discrete positions or configurations, with each position or configuration providing a different flow resistance and/or drainage rate relative to the other positions or configurations. Accordingly, the devices can be incrementally adjusted through the positions or configurations until the desired flow resistance and/or drainage rate is achieved. Once the desired flow resistance and/or drainage rate is achieved, the devices are configured to maintain the set position or configuration until further input. In some embodiments, various components of the devices operate as a ratchet mechanism, which enables the incremental adjustments of the devices between the plurality of positions or configurations, and can hold or lock the device in the desired position or configuration.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1A-7C.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%. Reference throughout this specification to the term "resistance" refers to fluid resistance unless the context clearly dictates otherwise. The terms "drainage rate," "flow rate," and "flow" are used interchangeably to describe the movement of fluid through a structure.

Although certain embodiments herein are described in terms of shunting fluid from an anterior chamber of an eye, one of skill in the art will appreciate that the present technology can be readily adapted to shunt fluid from and/or between other portions of the eye, or, more generally, from and/or between a first body region and a second body region. Moreover, while the certain embodiments herein are described in the context of glaucoma treatment, any of the embodiments herein, including those referred to as "glaucoma shunts" or "glaucoma devices" may nevertheless be used and/or modified to treat other diseases or conditions, including other diseases or conditions of the eye or other body regions. For example, the systems described herein can be used to treat diseases characterized by increased pressure and/or fluid build-up, including but not limited to heart failure (e.g., heart failure with preserved ejection fraction, heart failure with reduced ejection fraction, etc.), pulmonary failure, renal failure, hydrocephalus, and the like. Moreover, while generally described in terms of shunting aqueous, the systems described herein may be applied equally to shunting other fluid, such as blood or cerebrospinal fluid, between the first body region and the second body region.

The headings provided herein are for convenience only and do not interpret the scope or meaning of the claimed present technology.

A. Intraocular Shunts for Glaucoma Treatment

Glaucoma refers to a group of eye diseases associated with damage to the optic nerve which eventually results in vision loss and blindness. As noted above, glaucoma is a degenerative ocular condition characterized by an increase in pressure within the eye resulting from an increase in production of aqueous within the eye and/or a decrease in the rate of outflow of aqueous from within the eye into the blood stream. The increased pressure leads to injury of the optic nerve over time. Unfortunately, patients often do not present with symptoms of increased intraocular pressure until the onset of glaucoma. As such, patients typically must be closely monitored once increased pressure is identified even if they are not symptomatic. The monitoring continues over the course of the disease so clinicians can intervene early to stem progression of the disease. Monitoring pressure requires patients to visit a clinic site on a regular basis which is expensive, time-consuming, and inconvenient. The early stages of glaucoma are typically treated with drugs (e.g., eye drops) and/or laser therapy. When drug/laser treatments no longer suffice, however, surgical approaches can be used. Surgical or minimally invasive approaches primarily attempt to increase the outflow of aqueous from the anterior chamber to the blood stream either by the creation of alternative fluid paths or the augmentation of the natural paths for aqueous outflow.

Figure 1B:
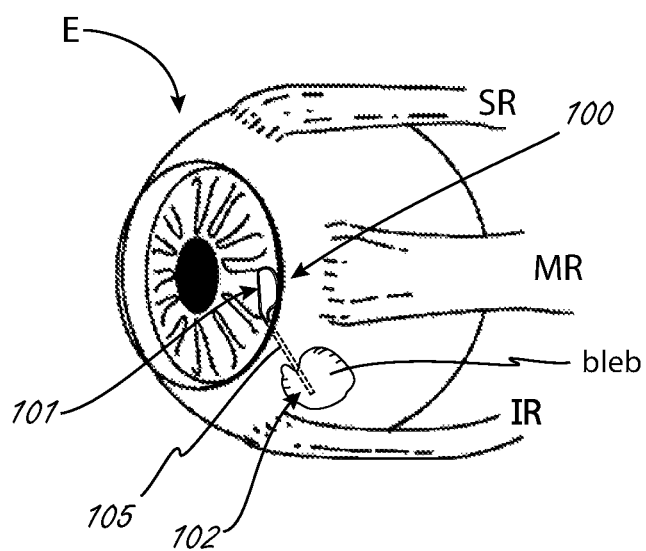
FIG. 1B is an isometric view of the eye and implanted shunt of FIG. 1A.

FIGS. 1A and 1B illustrate a human eye E and suitable location(s) in which a shunt may be implanted within the eye E in accordance with embodiments of the present technology. More specifically, FIG. 1A is a simplified front view of the eye E with an implanted shunt 100, and FIG. 1B is an isometric view of the eye E and the shunt 100 of FIG. 1A. Referring first to FIG. 1A, the eye E includes a number of muscles to control its movement, including a superior rectus SR, inferior rectus IR, lateral rectus LR, medial rectus MR, superior oblique SO, and inferior oblique IO. The eye E also includes an iris, pupil, and limbus.

Referring to FIGS. 1A and 1B together, the shunt 100 can have a drainage element 105 (e.g., a drainage tube) positioned such that an inflow portion 101 is positioned in an anterior chamber of the eye E, and an outflow portion 102 is positioned at a different location within the eye E, such as a bleb space. The shunt 100 can be implanted in a variety of orientations. For example, when implanted, the drainage element 105 may extend in a superior, inferior, medial, and/or lateral direction from the anterior chamber. Depending upon the design of the shunt 100, the outflow portion 102 can be placed in a number of different suitable outflow locations (e.g., between the choroid and the sclera, between the conjunctiva and the sclera, etc.).

Outflow resistance can change over time for a variety of reasons, e.g., as the outflow location goes through its healing process after surgical implantation of a shunt (e.g., shunt 100) or further blockage in the drainage network from the anterior chamber through the trabecular meshwork, Schlemm's canal, the collector channels, and eventually into the vein and the body's circulatory system. Accordingly, a clinician may desire to modify the shunt after implantation to either increase or decrease the outflow resistance in response to such changes or for other clinical reasons. For example, in many procedures the shunt is modified at implantation to temporarily increase its outflow resistance. After a period of time deemed sufficient to allow for healing of the tissues and stabilization of the outflow resistance, the modification to the shunt is reversed, thereby decreasing the outflow resistance. In another example, the clinician may implant the shunt and after subsequent monitoring of intraocular pressure determine a modification of the drainage rate through the shunt is desired. Such modifications can be invasive, time-consuming, and/or expensive for patients. If such a procedure is not followed, however, there is a high likelihood of creating hypotony (excessively low eye pressure), which can result in further complications, including damage to the optic nerve. In contrast, intraocular shunting systems configured in accordance with embodiments of the present technology allow the clinician to selectively adjust the flow of fluid through the shunt after implantation without additional invasive surgical procedures.

The shunts described herein can be implanted having a first drainage rate and subsequently remotely adjusted to achieve a second, different drainage rate. The adjustment can be based on the needs of the individual patient. For example, the shunt may be implanted at a first lower flow rate and subsequently adjusted to a second higher flow rate as clinically necessary. The shunts described herein can be delivered using either ab interno or ab externo implant techniques, and can be delivered via needles. The needles can have a variety of shapes and configurations to accommodate the various shapes of the shunts described herein. Details of the implant procedure, the implant devices, and bleb formation are described in greater detail in International Patent Application No. PCT/US20/41152, the disclosure of which is incorporated by reference herein for all purposes.

In many of the embodiments described herein, the flow control assemblies are configured to introduce features that selectively impede or attenuate fluid flow through the shunt during operation. In this way, the flow control assemblies can incrementally or continuously change the flow resistance through the shunt to selectively regulate pressure and/or flow. The flow control assemblies configured in accordance with the present technology can accordingly adjust the level of interference or compression between a number of different positions, and accommodate a multitude of variables (e.g., IOP, aqueous production rate, native aqueous outflow resistance, and/or native aqueous outflow rate) to precisely regulate flow rate through the shunt.

The disclosed flow control assemblies can be operated using energy. This feature allows such devices to be implanted in the patient and then modified/adjusted over time without further invasive surgeries or procedures for the patient. Further, because the devices disclosed herein may be actuated via energy from an external energy source (e.g., a laser), such devices do not require any additional power to maintain a desired orientation or position. Rather, the actuators/fluid resistors disclosed herein can maintain a desired position/orientation without power. This can significantly increase the usable lifetime of such devices and enable such devices to be effective long after the initial implantation procedure.

B. Operation of Actuation Elements

Some embodiments of the present technology include actuation assemblies (e.g., flow control assemblies, flow control mechanisms, etc.) that have at least one actuation element coupled to a moveable element (e.g., an arm, a control element, a gating element, a flow control element, a rack element etc.). As described in detail below, the moveable element can be formed to interface with a lumen (FIGS. 2A-4D) and/or interface with (e.g., at least partially block) a port providing inflow or outflow to a lumen (FIGS. 5A-5D and 7A-7C). Movement of the actuation element(s) generates (e.g., translational and/or rotational) movement of the moveable element.

The actuation element(s) can include a shape memory material (e.g., a shape memory alloy, or a shape memory polymer). Movement of the actuation element(s) can be generated through applied stress and/or use of a shape memory effect (e.g., as driven by a change in temperature). The shape memory effect enables deformations that have altered an element from its preferred geometric configuration (e.g., original or fabricated configuration, shape-set configuration, heat-set configuration, etc.) to be largely or entirely reversed during operation of the actuation assembly. For example, thermal actuation (heating) can reverse deformation(s) by inducing a change in state (e.g., phase change) in the actuator material, inducing a temporary elevated internal stress that promotes a shape change toward the preferred geometric configuration. For a shape memory alloy, the change in state can be from a martensitic phase (alternatively, R-phase) to an austenitic phase. For a shape memory polymer, the change in state can be via a glass transition temperature or a melting temperature. The change in state can reverse deformation(s) of the material—for example, deformation with respect to its preferred geometric configuration—without any (e.g., externally) applied stress to the actuation element. That is, a deformation that is present in the material at a first temperature (e.g., body temperature) can be (e.g., thermally) recovered and/or altered by raising the material to a second (e.g., higher) temperature. Upon cooling (and changing state, e.g., back to martensitic phase), the actuation element retains its preferred geometric configuration. With the material in this relatively cooler-temperature condition it may require a lower force or stress to thermoelastically deform the material, and any subsequently applied external stress can cause the actuation element to once again deform away from the original geometric configuration.

The actuation element(s) can be processed such that a transition temperature at which the change in state occurs (e.g., the austenite start temperature, the austenite final temperature, etc.) is above a threshold temperature (e.g., body temperature). For example, the transition temperature can be set to be about 45 deg. C., about 50 deg. C., about 55 deg. C., or about 60 deg. C. In some embodiments, the actuator material is heated from body temperature to a temperature above the austenite start temperature (or alternatively above the R-phase start temperature, the austenite finish temperature, or the R-phase finish temperature) such that an upper plateau stress (e.g., "UPS_body temperature") of the material in a first state (e.g., thermoelastic martensitic phase, or thermoelastic R-phase at body temperature) is lower than an upper plateau stress (e.g., "UPS_actuated temperature") of the material in a heated state (e.g., superelastic state), which achieves partial or full free recovery. For example, the actuator material can be heated such that UPS_actuated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase at body temperature) is lower than a lower plateau stress (e.g., "LPS") of the material in a heated state (e.g., superelastic state), which achieves partial or full free recovery. For example, the actuator material can be aged such that LPS_activated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase) is higher than a lower plateau stress of the material in a heated state, which achieves partial free recovery. For example, the actuator material can be aged such that LPS_activated temperature<UPS_body temperature.

The actuation assembly can be formed such that the actuation elements have substantially the same preferred geometric configuration (e.g., memory shape, or length, $L_0$). The actuation assembly can be assembled such that, upon introduction into a patient (e.g., implantation), at least one (e.g., a first) actuation element/shape memory element has been deformed with respect to its preferred geometric configuration (e.g., to have $L_1 \neq L_0$), while at least one other opposing (e.g., a second) actuation element/shape memory element positioned adjacent to the first actuation element is substantially at its preferred geometric configuration (e.g., $L_0$). In other embodiments, however, both the first and second actuation elements may be deformed with respect to their corresponding preferred geometric configuration upon introduction into the patient (e.g., the first actuation element is contracted relative to its preferred geometric configuration and the second actuation element is expanded relative to its preferred geometric configuration).

In some embodiments of the present technology, $L_1 > L_0$—for example, the deformed first actuation element is elongated with respect to its preferred "shape memory" length. In some embodiments, $L_1 < L_0$—for example, the deformed first actuation element is compressed with respect to its preferred shape memory length. The actuation assembly can be formed such that, in operation, its overall dimension (e.g., overall length) is substantially fixed (e.g., $L_0+L_1=$ a constant). For example, (e.g., outermost) ends of the actuation elements can be fixed, such that movement of the actuation elements occurs between the points of fixation. The overall geometry of the actuation elements, along with the lengths, can be selected such that, in operation, deformation within the actuation elements remains below about 10%, about 9%, about 8%, about 7%, about 6%, about 5%, about 4%, about 3%, about 2%, or about 1%.

The (e.g., first and second) actuation elements are arranged such that a movement (e.g., deflection or deformation) of the first actuation element/first shape memory element is accompanied by (e.g., causes) an opposing movement of the second actuation element/second shape memory element. The movement can be a deflection or a deformation. In operation, selective heating of the first actuation element of the actuation assembly causes it to move to and/or toward its preferred geometric configuration (e.g., revert from $L_1$ to $L_0$), moving the coupled moveable element. At the same time, movement of the first actuation element causes a corresponding movement of the second actuation element in an opposite direction. For example, a contraction of the first actuation element is accompanied by (e.g., causes) an elongation of the second actuation element (e.g., from $L_0$ to $L_1$). The second actuation element is not heated (e.g., remains at body temperature), and therefore the second actuation element deforms (e.g., remains martensitic and elongates). The first actuation element cools following heating, and returns to an LPS state in which it moves to a point of equilibrium relative to the second actuation element. To reverse the configuration of the actuation assembly (e.g., the position of the moveable element), the second actuation element is heated to move to and/or toward its preferred geometric configuration (e.g., from $L_1$ to $L_0$). The return of the second actuation element toward its preferred geometric configuration causes the moveable element to move back to its prior position, and elongates the first actuation element (e.g., from $L_0$ to $L_1$) in turn. The position of the moveable element for the actuation assembly can be repeatably toggled (e.g., between open and closed) by repeating the foregoing operations. The heating of an actuation element can be accomplished via application of incident energy (e.g., via a laser or inductive coupling). Further, as mentioned above, the source of the incident energy may be external to the patient (e.g., non-invasive).

C. Adjustable Glaucoma Shunts

Some embodiments of the present technology are directed to adjustable devices for treating glaucoma. The devices can include a drainage element having a lumen extending therethrough for draining aqueous from the anterior chamber. Some embodiments include an actuation assembly that can drive movement of a flow control element to change the flow resistance through the lumen, thereby increasing or decreasing the relative drainage rate of aqueous from the anterior chamber. In particular, some embodiments of the present technology provide adjustable devices that are selectively titratable to provide various levels of therapy. For example, the devices can be adjusted through a number of positions or configurations, with each position or configuration representing a different relative flow resistance and/or drainage rate relative to the other positions or configurations. Accordingly, the devices can be incrementally adjusted until the desired flow resistance and/or drainage rate is achieved. Once achieved, the devices are configured to maintain the set position or configuration until further input. In some embodiments, various components of the devices operate as a ratchet mechanism, which promote the incremental adjustments of the devices between the plurality of positions or configurations, and can hold or lock the device in the desired position or configuration.

Figure 2:
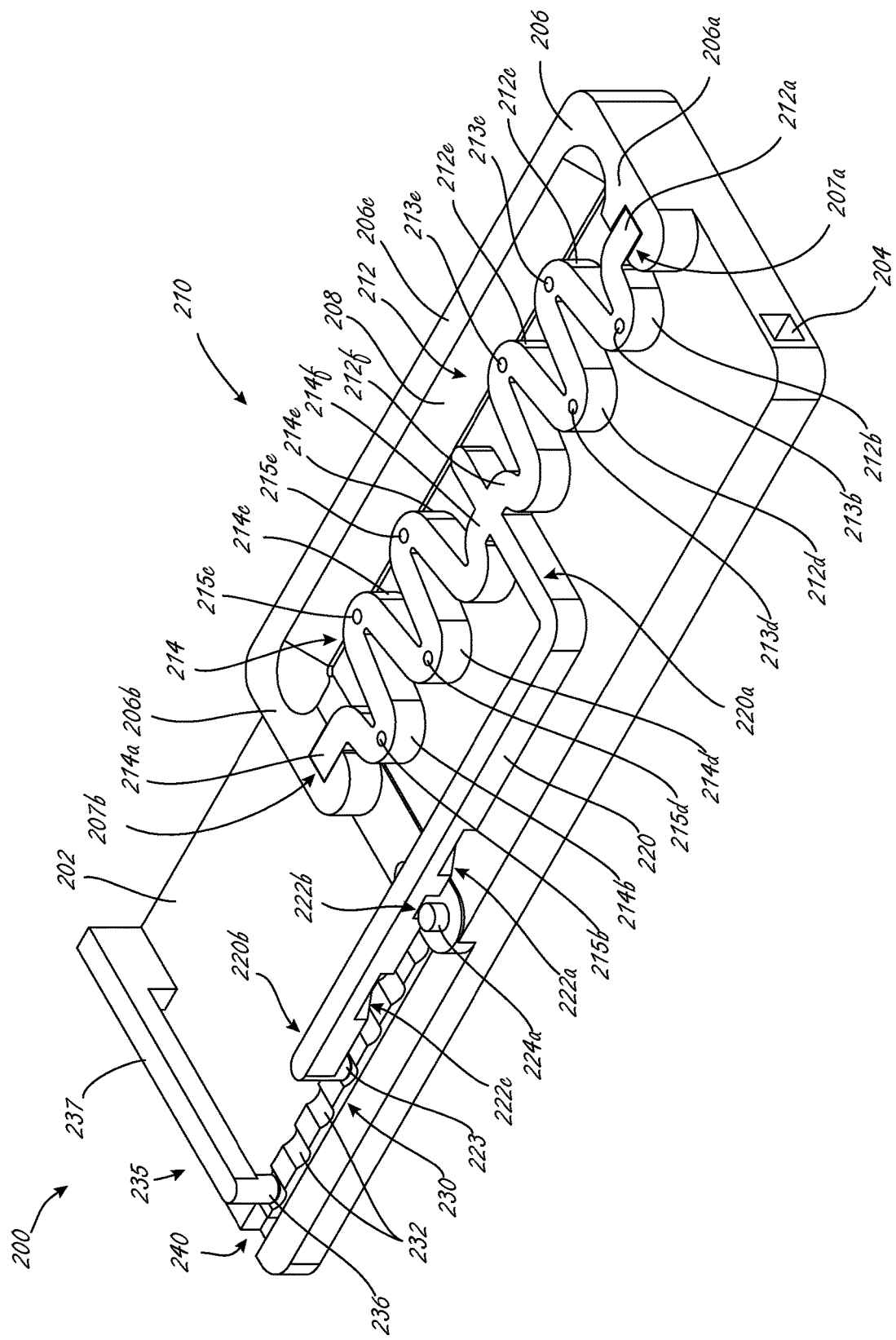
FIG. 2 is a perspective view of an adjustable glaucoma treatment device configured in accordance with select embodiments of the present technology.
Figure 4A:
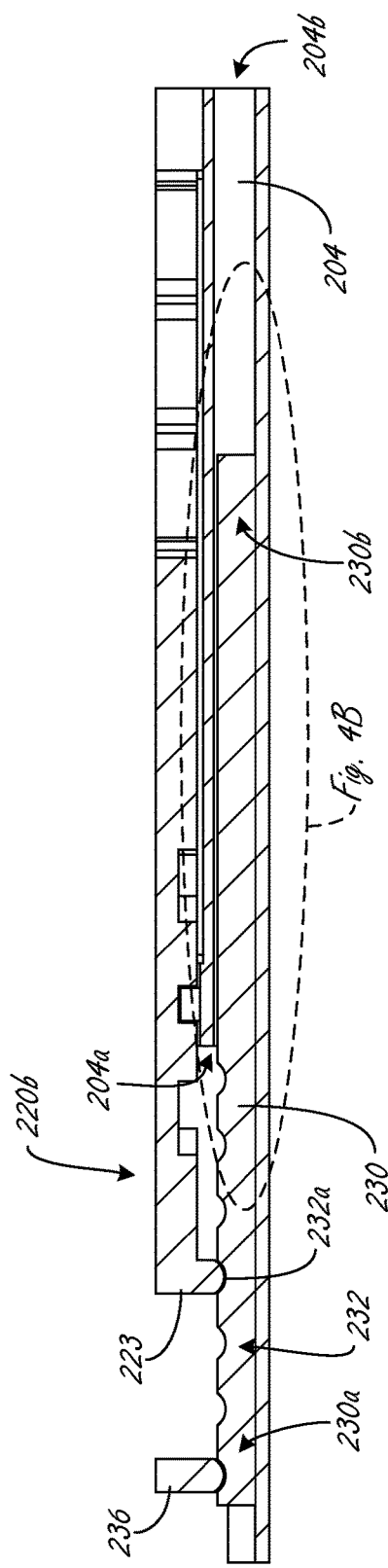
FIGS. 4A-4D illustrate the adjustable glaucoma treatment device shown in FIG. 2 in two different configurations in accordance with select embodiments of the present technology.

FIG. 2 illustrates an adjustable glaucoma treatment device 200 ("device 200") configured in accordance with select embodiments of the present technology. The device 200 includes a base 202 (e.g., a plate) and a lumen 204 extending through at least a portion of the base 202. The lumen 204 extends between an inflow port 204a positionable within an anterior chamber and an outflow port 204b positionable within a desired outflow location, such as a bleb space (FIG. 4A). As described in greater detail below, the base 202 comprises an at least partially solid structure that provides a mounting surface for various components of the device 200. The base 202 can be composed of any biocompatible material suitable for implantation into a human eye and/or include a biocompatible coating. When implanted into an eye of a patient, the device 200 is configured to drain aqueous from an anterior chamber of the eye to a desired outflow location (e.g., a bleb space). Accordingly, in at least some embodiments, the lumen 204 is configured for fluid communication with the anterior chamber of the eye to receive fluid therefrom.

The device 200 includes a frame 206 extending from the base 202 (e.g., as a ridge or other feature offset from a surface of the base 202). The frame 206 includes a first anchoring element 206a, a second anchoring element 206b, and a spine 206c extending therebetween. In some embodiments, the first anchoring element 206a and the second anchoring element 206b can extend from and are generally perpendicular to opposing end portions of the spine 206c. In the illustrated embodiment, the spine 206c is at least partially offset from a laterally extending central axis of the device 200, and the first anchoring element 206a and the second anchoring element 206b extend generally toward the laterally extending central axis of the device 200. In some embodiments, and as described in greater detail below, the spine 206c can optionally have a deflective surface 208 that is configured to redirect (e.g., reflect or refract) energy (e.g., laser energy) from an energy source positioned external to the eye to an actuation assembly 210. In some embodiments, the frame 206 can be secured to, or integral with, the base 202 such that the frame 206 does not move relative to the base 202 when the device 200 is adjusted.

The device 200 further includes an actuation assembly 210, an arm 220, and a rack element 230. In some embodiments, the actuation assembly 210, the arm 220, and the rack element 230 together operate as a ratchet mechanism for selectively changing a shape and/or size (e.g., a length, a width, or other dimension) of the lumen 204, and/or for selectively changing a flow resistance through the lumen 204. For example, as described in greater detail below, the actuation assembly 210 can move the arm 220 and the rack element 230 through a plurality of positions. As described with respect to FIGS. 4A-4C, at least a portion of the rack element 230 can be positionable within the lumen 204 such that actuation of the actuation assembly 210 moves the rack element 230 relative to the lumen 204 and changes the flow resistance through the lumen 204. Accordingly, the actuation assembly 210, the arm 220, and the rack element 230 enable a user to selectively adjust therapy provided by the device 200.

The actuation assembly 210 can include a first actuation element 212 and a second actuation element 214. The first actuation element 212 and the second actuation element 214 can at least partially resemble a flat (e.g., linear) spring, and can therefore have a generally serpentine or curved shape with a number of expandable and contractable bend regions. For example, in the illustrated embodiment, the first actuation element 212 includes a first end portion 212a, a first bend region 212b, a second bend region 212c, a third bend region 212d, a fourth bend region 212e, and a second end portion 212f. Likewise, the second actuation element 214 includes a first end portion 214a, a first bend region 214b, a second bend region 214c, a third bend region 214d, a fourth bend region 214e, and a second end portion 214f In other embodiments, however, the first actuation element 212 and/or the second actuation element 214 can have a different number of bend regions than illustrated in FIG. 2. For example, the first actuation element 212 and/or the second actuation element 214 can have one, two, three, four, five, or more bend regions. As described in detail below, the actuation elements 212, 214 are configured to expand and/or contract at their respective bend regions as the actuation assembly 210 is actuated.

The first actuation element 212 extends generally between the first anchoring element 206a and the arm 220. For example, the first end portion 212a of the first actuation element 212 can be received within a first notch 207a (e.g., via a friction fit) of the first anchoring element 206a, and the second end portion 212f can be connected to the arm 220 at the first end portion 220a. The second actuation element 214 extends generally between the second anchoring element 206b and the arm 220. For example, the first end portion 214a of the second actuation element 214 can be received within a second notch 207b (e.g., via a friction fit) of the second anchoring element 206b, and the second end portion 212f can be connected to the arm 220 at the first end portion 220a. Accordingly, the first end portion 220a of the arm 220 is generally between the first actuation element 212 and the second actuation element 214.

As described above in Section B, the first actuation element 212 and the second actuation element 214 can comprise shape-memory material(s) configured to at least partially transition from a first phase/state (e.g., a martensitic or intermediate state) to a second phase/state (e.g., an intermediate or austenitic state) upon application of energy. In some embodiments, for example, the first actuation element 212 and the second actuation element 214 can be composed of a shape memory alloy such as nitinol. In some embodiments, the phase change corresponds with a dimensional change of the actuation element. The first actuation element 212 and the second actuation element 214 can therefore change shape (e.g., expand and/or contract in length, width, etc.) in response to exposure to energy, such as light, heat, and the like, that creates a temperature increase in the material. In such embodiments, the actuation assembly 210 can be selectively actuated by applying energy directly or indirectly to the first actuation element 212 and/or the second actuation element 214. In some embodiments, the energy can be applied from an energy source positioned external to the eye (e.g., a laser). In some embodiments, one or more heating wires can be run through or wound around at least a portion of the actuation elements, and the energy can be applied by operating at least one of the heating wires to provide resistive heating to the desired actuation element. In some embodiments, the actuation assembly 210 can be remotely actuated.

The first actuation element 212 and the second actuation element 214 generally act in opposition as the actuation assembly 210 is actuated. However, the distance between the first anchoring element 206a and the second anchoring element 206b does not change as the actuation assembly 210 is actuated. Accordingly, actuation of the first actuation element 212 to cause a first shape change in the first actuation element 212 causes a corresponding deformation or second shape change in the second actuation element 214. For example, when the first actuation element 212 is actuated (e.g., via heat), the first actuation element 212 may straighten out (e.g., lengthen, expand, etc.) at one or more bend regions 212b-e, thereby increasing a distance between two adjacent bend regions 212b-e. Because the first anchoring element 206a is secured to the base 202 and does not move as the first actuation element 212 changes shape, the second actuation element 214 is compressed at one or more bend regions 214b-e to account for the shape change of the first actuation element 212. This causes a distance between two adjacent bend regions 214b-e to be reduced and pushes the first end portion 220a of the arm 220 toward the second anchoring element 206b. This movement can be reversed when the second actuation element 214 is actuated (e.g., heated). For example, when the second actuation element 214 is actuated, the second actuation element 214 may straighten out (e.g., lengthen, expand, etc.) at one or more bend regions 214b-e, thereby increasing a distance between two adjacent bend regions 214b-e. Because the second anchoring element 206b is secured to the base 202 and does not move as the second actuation element 214 changes shape, the first actuation element 212 is compressed at one or more bend regions 212b-e to account for the shape change of the second actuation element 214. This causes a distance between two adjacent bend regions 212b-e to be reduced and pushes the first end portion 220a of the arm 220 back toward the first anchoring element 206a. Although described as lengthening when actuated, the first and second actuation elements 212, 214 can alternatively be under tension (e.g., lengthened) relative to their preferred geometries, such that actuation of the first or second actuation element 212, 214 causes the actuation element to contract (e.g., shorten).

In some embodiments, the individual bend regions 212b-e on the first actuation element 212 and the individual bend regions 214b-e on the second actuation element 214 can be individually targeted to increase the granularity of actuation. In some embodiments, the individual bend regions 212b-e can include corresponding targets 213b-e. Likewise, the individual bend regions 214b-e can include corresponding targets 215b-e. The targets 213b-e and 215b-e can be recesses, wells, channels, divots, or other features configured to promote penetration of energy into the corresponding bend region of the actuation element to thereby provide a relatively more even heating of the full thickness of the actuation element 212 or 214 at the targeted bend region. For example, the target 213b is a cylindrical recess that extends at least partially into the first actuation element 212 at the first bend region 212b. Applying energy to the target 213b is expected to provide more even heating through the full thickness of the first actuation element 212 at the first bend region 212b (as opposed to just heating the surface of the first actuation element 212). Without being bound by theory, the relatively even application of energy throughout the full thickness of various regions of the actuation elements 212 and 214 is expected to increase the reproducibility and consistency of motion of the actuation elements 212 and 214, which in turn is expected to increase the precision of adjustments to the lumen 204.

In some embodiments, the targets 213b-e and 215b-e can comprise a material or coating that is more absorptive than the portions of the bend regions and actuation elements surrounding the targets. For example, the targets 213b-e and 215b-e can be oxidized using titanium oxides and the like to create a "darkening" effect that makes the targets 213b-e and 215b-e absorb energy more readily than the surrounding regions. By being more absorptive, the targets 213b-e and 215b-e retain more energy and are heated more readily than the surrounding regions, permitting selective actuation of the individual bend regions corresponding to the targets 213b-e and 215b-e without inducing substantial phase and/or shape change in the surrounding material. In such embodiments, the targets 213b-e and 215b-e may cover a larger surface area of the corresponding bend region than illustrated in FIG. 2 (e.g., the oxidized surface occupies the entire bend region). Without being bound by theory, making the targets 213b-e and 215b-e more absorptive than the surrounding regions is expected to increase the granularity and consistency of motion of the actuation elements 212 and 214, which in turn is expected to increase the precision of adjustments to the lumen 204. In some embodiments, the material or coating may further provide an insulating effect that reduces energy transfer between the actuation elements 212, 214 and their surrounding environment.

In some embodiments, portions of the first actuation element 212 between adjacent targets 213b-e and portions of the second actuation element 214 between adjacent targets 215b-e can comprise a material or coating that is more reflective than the targets 213b-e and 215b-e themselves. This can be true regardless of whether the targets 213b-e and 215b-e themselves have a coating or have otherwise been treated to increase their absorptiveness. In such embodiments, energy received at the reflective portions between the targets 213b-e and 215b-e is generally reflected and does not substantially heat the corresponding actuation element. In some embodiments, however, energy received at the targets 213b-e and 215b-e can indirectly heat the surrounding reflective portions. Without being bound by theory, making the regions between the targets 213b-e and 215b-e more reflective than the targets 213b-e and 215b-e is expected to increase the granularity and consistency of motion of the actuation elements 212 and 214, which in turn is expected to increase the precision of the adjustments to the lumen 204.

The rack element 230 can be a moveable linear rack having a plurality of teeth 231 and a plurality of corresponding grooves 232 between the plurality of teeth 231, although other suitable configurations are within the scope of the present technology. In some embodiments, for example, the rack element 230 can be a sawtooth wire or other suitable feature that provides a friction interface with the engagement element 223. A distal end portion (not shown) of the rack element 230 can be positioned at least partially within the lumen 204 (FIGS. 4A-4D). The rack element 230 can include two, three, four, five, six, seven, eight, or more grooves 232. As will be appreciated by one skilled in the art in view of the following description, increasing the number of grooves 232 on the rack element 230 generally increases the number of discrete positions the rack element 230 can occupy. The number of grooves 232 may be increased by increasing an overall length of the rack element 230 and/or decreasing the spacing between adjacent grooves 232 (e.g., increasing a pitch of the grooves 232). Increasing a pitch of the grooves 232 may also generally increase the granularity of potential flow resistance adjustments by allowing for relatively smaller movements of the rack element 230.

In at least some configurations, the rack element 230 can be operably coupled to the actuation assembly 210 via the arm 220. As described in detail below with reference to FIGS. 3A and 3B, the actuation assembly 210 can, via the arm 220, move the rack element 230 through a plurality of different positions. As described in detail below with respect to FIGS. 4A-4D, linear movement of the rack element 230 through the plurality of positions adjusts a relative flow resistance through the lumen 204. For example, and as described below, in some embodiments a portion of the rack element 230 itself (e.g., the distal end portion) can function as a flow control element that is configured to directly change a shape and/or size of the lumen 204, and/or directly change a flow resistance through the lumen. In such embodiments, the distal end portion can have a generally uniform cross-section (e.g., the distal end portion does not have grooves 232 and corresponding teeth 231). In other embodiments, the flow control element is independent from, but coupled to, the rack element 230. Accordingly, in various embodiments the rack element 230 can either directly engage the lumen 204 (e.g., by occupying a portion of and/or pressing upon the lumen 204) or indirectly engage the lumen 204 (e.g., by moving a plug, dam, or other flow control element to at least partially block and/or at least partially unblock the lumen 204).

The device 200 further includes a channel 240 that acts as a track for the rack element 230 such that movement of the rack element 230 is constrained to a predefined linear track. In some embodiments, and as illustrated in FIG. 2, the channel 240 can be an elongated recess in the base 202 that is sized and shaped to retain the rack element 230. As the actuation assembly 210 drives the rack element 230 through the plurality of positions, the rack element 230 can slide within a length of the channel 240. In other embodiments, however, the channel 240 is not necessarily an elongated recess but rather has another configuration suitable for constraining the rack element 230 to a predefined path of motion.

The arm 220 has a first end portion 220a coupled to the actuation assembly 210 and a second end portion 220b configured to engage the rack element 230. In the illustrated embodiment, the arm 220 is generally elbow or "L" shaped, although in other embodiments the arm 220 may have any other suitable shape (e.g., "T" shaped, "I" shaped, etc.). The second end portion 220b of the arm 220 includes an engagement element 223 (e.g., a pawl) that can fit within a groove 232 on the rack element 230. The engagement element 223 therefore can mechanically couple the arm 220 to the rack element 230 such that movement of the arm 220 causes a corresponding movement of the rack element 230. The second end portion 220b of the arm 220 further includes a first recess 222a, a second recess 222b, and a third recess 222c. As best, illustrated in FIG. 3B and described below, the first recess 222a and the third recess 222c can be formed at an acute angle relative to a longitudinal axis of the arm 220. As described in greater detail below, the first recess 222a, the second recess 222b, and the third recess 222c enable the second end portion 220b of the arm 220 to disengage from the rack element 230 as the actuation assembly 210 is actuated.

In some embodiments, the frame 206 includes a surface 208 configured to deflect (e.g., reflect and/or refract) energy toward the first actuation element 212 and/or the second actuation element 214. In such embodiments, the first actuation element 212 and/or the second actuation element 214 can be actuated by directing energy (e.g., from an energy source external to a patient) toward the surface 208 rather than directly toward the first actuation element 212 (e.g., at targets 213b-e) or the second actuation element (e.g., at targets 215b-e). In other embodiments, energy can be directed toward the surface 208 in addition to directing energy toward the first actuation element 212 or the second actuation element 214. As energy is applied to the surface 208, the surface 208 deflects the received energy and redirects it toward the corresponding actuation element to drive a shape change of the actuation element. In some embodiments, the surface 208 can include discrete targets or zones (not shown) that direct energy to corresponding individual bend regions 212*b-e* or 214*b-e*. In some embodiments, the first actuation element 212 (e.g., the targets 213*b-e*) and/or the second actuation element 214 (e.g., the targets 215*b-e*) are treated with an absorptive material or otherwise configured to absorb the deflected energy. Without being bound by theory, use of the surface 208 is expected to enable energy application to surface(s) of the actuation elements that may otherwise be blocked or hard to reach (e.g., a surface facing the base 202 and/or a surface facing a back portion of the eye). The surface 208 can comprise any material suitable for deflecting energy (e.g., laser energy). For example, the surface 208 can be composed of a material such as gold, palladium, platinum, or the like, and can be configured to reflect energy, such as visible and/or infrared electromagnetic radiation. In another example, the surface 208 can be composed of a material such as glass, and can be configured to refract energy, such as visible and/or infrared electromagnetic radiation.

In some embodiments, the deflective surface 208 extends from or is otherwise at least partially spaced apart from the frame 206. For example, the deflective surface 208 can be a prism, mirror, or other refractive or reflective structure that, rather than being directly carried by the frame 206, is tethered to the frame 206 or de-coupled from the frame. In such embodiments, the deflective surface 208 can be used in a similar manner as described above to indirectly drive actuation of the actuation elements 212, 214. However, in such embodiments, the majority (or entirety) of the frame 206 can be placed within the eye but outside the anterior chamber (e.g., external, in the sclera or another region not directly accessible via laser energy) while the deflective surface 208 is positioned within the anterior chamber (e.g., such that it is accessible via laser energy). The actuation elements 212, 214 can be actuated by applying energy (e.g., laser energy) to the deflective surface 208 positioned in the anterior chamber, which then redirects the energy toward the actuation elements 212, 214 positioned substantially external to the anterior chamber. Without being bound by theory, spacing the deflective surface 208 apart from the frame 206 therefore enables a substantial portion of the device 200 to remain external to the anterior chamber, which in turn may reduce associated complications (e.g., endothelial cell loss).

The device 200 can further include a first blocking element 224*a* and a second blocking element (not shown) positioned on an opposite side of the arm 220 from the first blocking element 224*a*. The first blocking element 224*a* and the second blocking element can be a knob, tab, or other feature that prevents the arm 220 from disengaging from the rack element 230 in at least some configurations. However, the first blocking element 224*a* and the second blocking element are sized and shaped such that they can fit through at least one of the recesses (the first recess 222*a*, the second recess 222*b*, and/or the third recess 222*c*) on the arm 220. As described in detail below, this permits the arm 220 to disengage from the rack element 230 during actuation of the actuation assembly 210.

The device 200 can further include a locking mechanism 235 comprising an immobilized arm 237 having a locking element 236 (e.g., a pawl) that fits into a groove 232 on the rack element 230. The immobilized arm 237 can be secured to or integral with the base 202 such that the immobilized arm 237 does not move with respect to the base 202. The locking element 236 can prevent movement of the rack element 230 in the channel 240 when the arm 220 becomes disengaged from the rack element 230, as described below with respect to FIG. 3. In some embodiments, the force needed to move the locking element 236 out of the corresponding groove 232 is less than the force needed to move the engagement element 223 of the arm 220 out of the corresponding groove 232. Accordingly, when the actuation assembly 210 is actuated, the engagement element 223 initially remains in the same groove 232 and moves the rack element 230 while the locking element 236 moves into a different groove than it was originally in. However, once the arm 220 disengages from the rack element 230, the locking element 236 remains in the same groove 232 and prevents further movement of the rack element 230.

In some embodiments, the immobilized arm 237 can comprise shape-memory material(s) configured to at least partially transition from a first phase/state (e.g., a martensitic or R-phase state) to a second phase/state (e.g., a R-phase or austenitic state) upon application of energy. In some embodiments, for example, the immobilized arm 237 can be composed of a shape memory alloy such as nitinol. In some embodiments, the phase change corresponds with a dimensional change (e.g., length, width, etc.) of the immobilized arm 237. For example, the immobilized arm 237 can be moved from a first position in which the locking element 236 is engaged with the rack element 230 (FIG. 2) and a second position in which the locking element 236 is disengaged from the rack element 230 (not shown). In such embodiments, the immobilized arm 237 can be selectively actuated such that it engages with the rack element 230 when the arm 220 is disengaged from the rack element 230, thereby preventing movement of the rack element 230. Similarly, the immobilized arm 237 can be selectively actuated such that is disengaged from the rack element 230 during actuation of the actuation assembly 210, thereby allowing movement of the rack element 230. By actively moving the locking mechanism 235 between engaged and disengaged positions, the force needed to disengage the rack element 230 from the locking mechanism 235 no longer needs to be less than the force needed to move the engagement element 223 of the arm 220 out of the corresponding groove 232. Rather, the locking mechanism 235 can simply be actively moved off the rack element 230 before actuating the actuation assembly 210.

The device 200 can include additional components or features not illustrated. In some embodiments, for example, the device 200 includes a cover or other feature configured to mate with the base 202 and provide a protective housing for at some aspects of the device 200, such as the actuation assembly 210, the arm 220, the rack element 230, and/or the locking mechanism 235. The cover can reduce and/or prevent bodily tissues from interfering with the function of the foregoing components. The device 200 can also include a funnel or inflow element that directs fluid (e.g., aqueous) to the input port 204*a* of the lumen 204. The device 200 may also include a drainage element that extends the lumen 204 to a desired drainage location (e.g., a bleb space). The drainage element can be a linear tubular element, a bent tubular element, or any other element that can transport fluid from the lumen 204 to a desired outflow location.

Figure 3A:
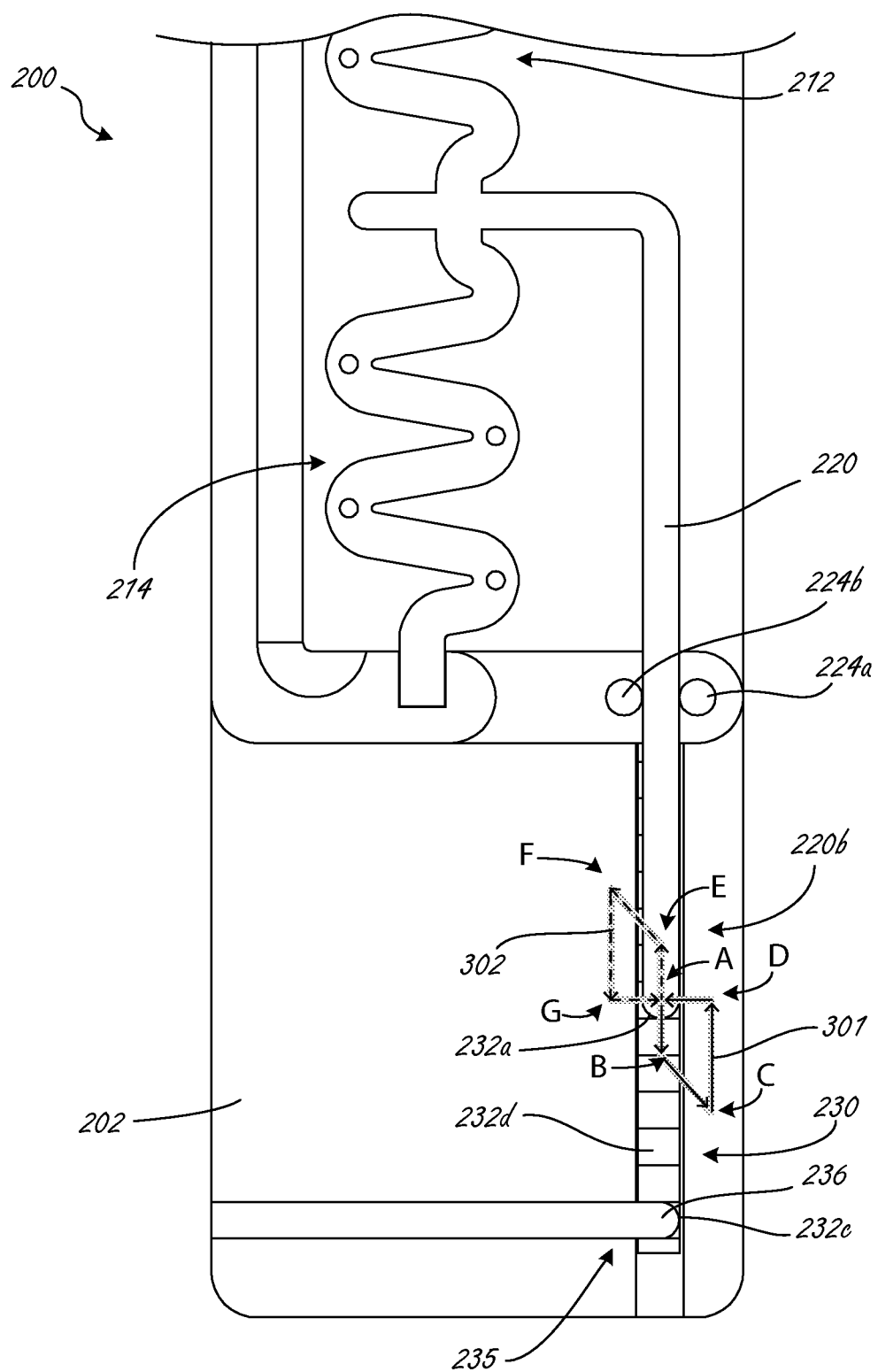
FIG. 3A is a front view of the adjustable glaucoma treatment device shown in FIG. 2 and illustrates a path of motion of an arm of the adjustable device in accordance with select embodiments of the present technology.

FIG. 3A illustrates a first path 301 (shown with solid arrows) and a second path 302 (shown with dashed arrows) that the arm 220 can move through during actuation of the actuation assembly 210. By way of example, when the first actuation element 212 is actuated, the arm 220 moves toward the locking mechanism 235. During this initial phase, the first blocking element 224a prevents non-linear movement of the arm 220 and instead forces the second end portion 220b of the arm 220 to move from position A to position B (e.g., along an axis extending parallel to an axial length of the second end portion 220b of the arm 220 and an axial length of the rack element 230). Due to the connection between the engagement element 223 and a first groove 232a, actuation of the first actuation element 212 initially causes the rack element 230 to slide with the arm 220 toward the locking mechanism 235. As described above, the fit between the locking element 236 and its corresponding groove 232 (e.g., a third groove 232c) is weaker than the fit between the engagement element 223 and the first groove 232a, so movement of the rack element 230 toward the locking mechanism 235 (position A to position B) causes the locking element 236 to disengage from the third groove 232c and move to a fourth groove 232d. As described above, this movement of the rack element 230 changes a characteristic of the lumen 204 to affect the flow of fluid therethrough.

Figure 3B:
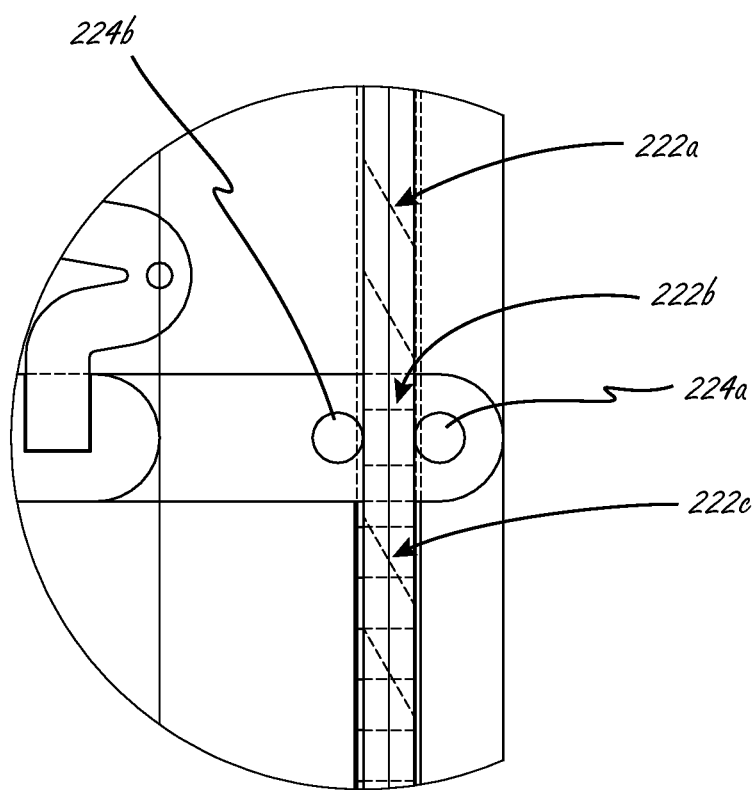
FIG. 3B is an enlarged view of a portion of the adjustable glaucoma treatment device shown in FIG. 2 and illustrates select features of the adjustable device in accordance with select embodiments of the present technology.

As the arm 220 moves toward position B, the first recess 222a (FIG. 3B) on the arm 220 aligns with the first blocking element 224a. Referring to FIG. 3B, the first recess 222a can extend through the arm 220 at an acute (e.g., non-perpendicular) angle relative to the longitudinal axis of the arm 220. The first recess 222a therefore receives the first blocking element 224a when the arm reaches position B. Returning to FIG. 3A, this causes the second end portion 220b of the arm 220 to disengage from the rack element 230 and swing outward to position C as the first blocking element 224a slides through the first recess 222a. When the second end portion 220b is in position C, the engagement element 223 is no longer positioned within the first groove 232a and the arm 220 is disengaged from the rack element 220. However, as described above, the rack element 230 retains its position due to engagement between the locking element 236 and the fourth groove 232d.

In some embodiments, the second end portion 220b remains in position C until further actuation of the actuation assembly 210. For example, once the first actuation element 212 is actuated to change shape (e.g., expand, lengthen, etc.) and causes the second end portion 220b to move from position A to position B to position C, the actuation assembly 210 can retain the position until further energy is input into the system (the actuation assembly 210 exhibits little to no recoil). In such embodiments, energy (heat) must be applied to the second actuation element 214 to drive the actuation assembly 210 back toward its original configuration, as described above with respect to FIG. 2. In such embodiments, when the second actuation element 214 is actuated to change shape (e.g., expand, lengthen, etc.), the second end portion 220b moves from position C to position D while the arm 220 remains disengaged from the rack element 230. At position D, the second recess 222b can align with the first blocking element 224a, permitting the arm 220 to swing back towards the rack element 230 and enabling the engagement element 223 to reengage the rack element 230 at a second groove 232 (not visible in FIG. 3A) that is different than the first groove 232a. At this point, the second end portion 220b of the arm returns to position A.

In some embodiments, the first actuation element 212 exhibits a partial or complete recoil or rebound effect (e.g., movement back to and/or toward its pre-actuated geometry). In such embodiments, once the applied energy (e.g., heat) has dissipated such that the first actuation element 212 has a temperature drop below its transition temperature, the first actuation element 212 is pushed back to and/or toward the shape it had before being energized. For example, once the first actuation element 212 returns to its pre-actuated thermoelastic material state (e.g., martensitic material state), a force applied by the second-actuation element 214 and/or another elastic element (e.g., a spring) against the first actuation element 212 can (e.g., automatically) drive the first actuation element 212 to and/or toward its pre-actuated shape. In such embodiments, the second actuation element 214 does not need to be actuated to move the second end portion 220b of the arm from position C to position D. Rather, the recoil of the first actuation element 212 causes the second end portion 220b of the arm to move from position C to position D (and thus back to position A once the second recess 222b aligns with the first blocking element 224a). In some embodiments, the recoil effect can be achieved by keeping the strain induced in the non-actuated actuation element (e.g., the second actuation element 214) below a threshold (e.g., below about 10%, below about 5%, etc.). Without being bound by theory, keeping the strain induced in the non-actuated actuation element below the threshold causes the non-actuated actuation element to re-assume the shape shown in FIG. 2 (e.g., its original shape) once the first actuation element 212 cools below its transition temperature. This resets the actuation assembly 210 to its original configuration shown in FIG. 2. As one skilled in the art will appreciate, the recoil effect may be achieved through manipulating the material properties in other suitable ways beyond those expressly disclosed herein. The recoil effect may also be achieved by including a spring or other elastomeric material that biases the first actuation element 212 toward its pre-actuated shape. The biasing force in the spring or other elastomeric material is generally low enough that, when the first actuation element 212 is heated above its transition temperature, the first actuation element 212 still undergoes a shape change when heated above the transition temperature (e.g., acting against the biasing force). However, the biasing force can be high enough to push the first actuation element 212 to and/or toward its pre-actuated shape after the first actuation element 212 has cooled below its transition temperature and returned to its pre-actuated thermoelastic material state (e.g., a martensitic material state).

Regardless of whether the actuation assembly 210 exhibits a recoil effect, the net result of the arm 220 moving along the first path 301 is movement of the rack element 230 in a first direction with respect to the base 202 and the lumen 204. For example, actuation of the actuation assembly 210 to move the arm 220 through the first path 301 may move the rack element 230 from a first position that imparts a first size, shape, and/or geometry on the lumen 204 to a second position that imparts a second size, shape, and/or geometry on the lumen 204 that is different than the first size, shape, and/or geometry. As a result, the first position can provide a first flow resistance through the lumen 204, and the second position can provide a second flow resistance through the lumen 204 that is different than the first flow resistance. Accordingly, when the device 200 is implanted in the eye, the actuation assembly 210 can be selectively actuated to change to change the flow resistance of the lumen 204, and thus change the drainage of aqueous from the anterior chamber.

The movement of the rack element 230, and therefore the change to the lumen 204, is reversible by moving the second end portion 220b of the arm through the second path 302. Movement of the arm 220 through the second path 302 occurs in a similar manner to movement of the arm 220 through the first path 301. For example, upon initial actuation of the second actuation element 214, the second end portion 220b of the arm 220 moves from position A to position E, sliding the rack element 230 along with it away from the locking mechanism 235 and toward the lumen 204. Once in position E, the third recess 222c (FIG. 3B) aligns with the second blocking element 224b, enabling the arm 220 to swing outward, disengage from the second groove 232 (not shown) of the rack element 230, and occupy position F. For example, referring to FIG. 3B, the third recess 222c can extend through the arm 220 at an acute (e.g., not perpendicular) angle relative to the longitudinal axis of the arm 220. The third recess 222c therefore receives the second blocking element 224b when the arm reaches position E, and further directs the arm 220 to swing outward to position F as the first blocking element 224a slides through the first recess 222a. Returning to FIG. 3A, once in position F, the arm 220 can automatically move toward position G (if the second actuation element 214 exhibits a recoil effect) or the first actuation element 212 can be actuated to move the arm to position G (if the actuation element does not exhibit a recoil effect). At position G, the second recess 222b aligns with the second blocking element 224b, permitting the arm 220 to reengage the rack element 230 at the first groove 232a. The net effect of the arm moving through the second path 302 is the movement of the rack element 230 in a second direction (e.g., toward the lumen 204) generally opposite the first direction the rack element 230 moved when the arm 220 went through the first path 301. For example, actuation of the actuation assembly 210 to move the arm 220 through the second path 302 can move the rack element 230 from the second position to the first position.

Although the foregoing describes the rack element 230 moving from a first position to a second position via movement of the arm through the first path 301 and moving from the second position back to the first position via movement of the arm through the second path 302, the device 200 is capable of moving between other configurations. For example, the arm 220 can be driven through the first path 301 multiple times without driving the arm 220 through the second path 302. Each time the arm 220 moves through the first path 301, the rack element 230 slides further in the first direction (e.g., further out of the lumen 204, as described in FIGS. 4A-4C). Likewise, the arm 220 can be driven through the second path 302 without first moving the arm 220 through the first path 301 to cause the rack element 230 to move in the second direction opposite the first direction (e.g., further into the lumen 204, as described in FIGS. 4A-4C). Accordingly, the rack element 230 can be selectively moved in opposite directions by selectively actuating the actuation assembly 210 to move the arm through the first path 301 and/or the second path 302, respectively. As described in greater detail in FIGS. 4A-4D, moving the rack element 230 in the first direction can reduce the flow resistance through the lumen 204, and moving the rack element 230 in the second direction can increase the flow resistance through the lumen 204.

FIGS. 4A-4D illustrate how linear movement of the rack element 230 changes a flow resistance through the lumen 204. FIG. 4A is a cross-sectional view of the device 200 in a first configuration and shows, among other things, the rack element 230 extending partially into the lumen 204. The rack element 230 includes a proximal end portion 230a and a distal end portion 230b. The proximal end portion 230a includes the plurality of grooves 232 for receiving the engagement element 223 of the arm 220. The plurality of grooves 232 remain generally unobstructed as the rack element 230 moves back and forth (i.e., the proximal end portion 230a generally does not extend into the lumen 204). In some embodiments, the proximal end portion 230a has a greater cross-sectional size (not shown) than the lumen 204. This is expected to prevent the proximal end portion 230a from entering the lumen 204 and ensure that the rack element 230 remains engaged with the locking element 236. In such embodiments, flow through the lumen 204 can be substantially reduced (e.g., stopped) by moving the proximal end portion 230a towards the lumen 204 until the proximal end portion 230a engages with and blocks an inflow port (e.g., inflow port 204a, FIG. 4B). Returning to the illustrated embodiment, the engagement element 223 is engaged with the proximal end portion 230a of the rack element 230 at a first groove 232a.

In at least some configurations, the distal end portion 230b of the rack element 230 can extend at least partially into the lumen 204. For example, the distal end portion 230b can enter the lumen 204 at an inflow port 204a and extend along a length of the lumen 204 towards an outflow port 204b. In some embodiments, the distal end portion 230b has a generally rectangular, circular, or other solid cross-sectional area that is generally similar in shape to an inner perimeter of the lumen (e.g., the distal end portion 230b does not include the plurality of grooves 232). In some embodiments, the distal end portion 230b can be tapered such that the cross-sectional area of the distal end portion 230b decreases moving from a first region adjacent the proximal end portion 230a to a second region spaced apart from the proximal end portion 230a. In such embodiments, the lumen 204 may also be tapered such that the distal end portion 230b and the lumen 204 form a needle valve. Incorporation of a needle valve like arrangement may increase the ability to change fluid resistance through the lumen 204 (e.g., the rate of change in flow resistance is non-linear). Regardless of the configuration, at least the distalmost end region of the distal end portion 230b can have a cross-sectional area that is less than the cross-sectional area of the lumen 204. Accordingly, even when the distal end portion 230b is within the lumen 204, fluid can still flow through the lumen 204.

Figure 4B:
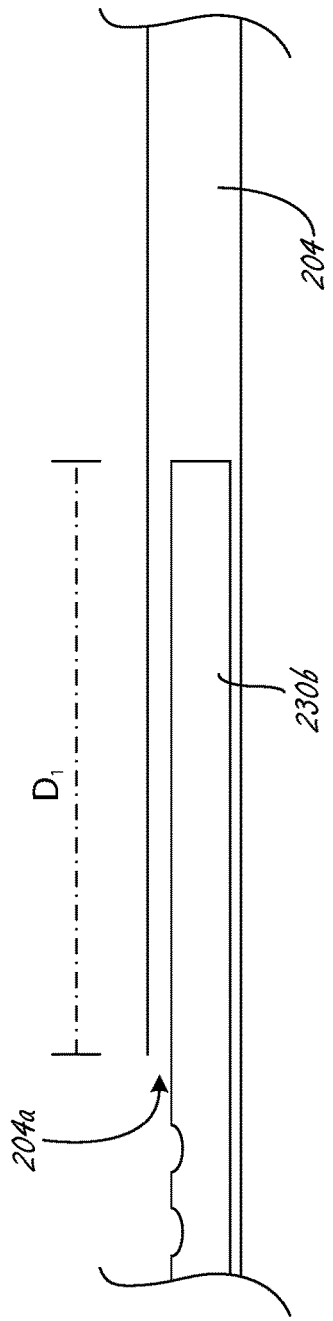

FIG. 4B, for example, is an enlarged view of the portion of the device 200 indicated in FIG. 4A. As illustrated, the distal end portion 230b extends into the lumen 204. In particular, the distal end portion 230b extends into the lumen by a distance $D_1$, as measured from the inflow port 204a. While the distal end portion 230b occupies some or even a substantial volume of the lumen 204, fluid can still flow from the inflow port 204a to the outflow port 204b around the distal end portion 230b.

Figure 4C:
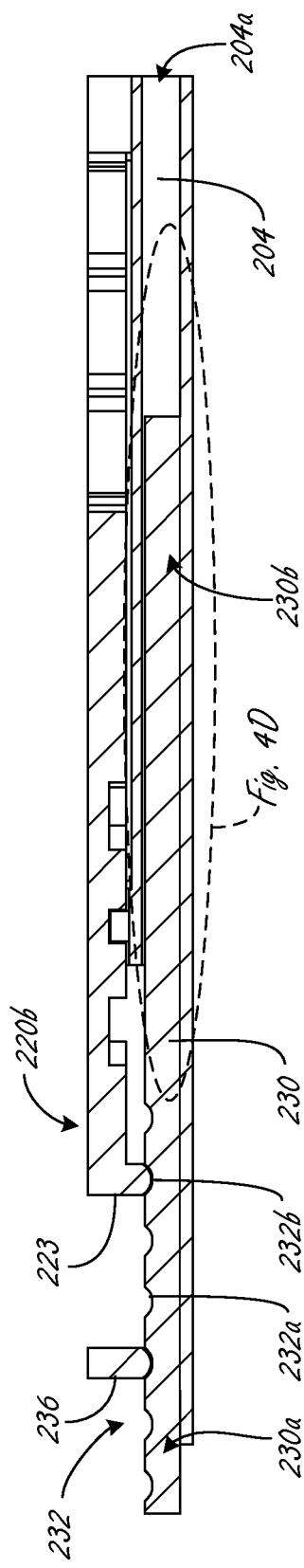
Figure 4D:
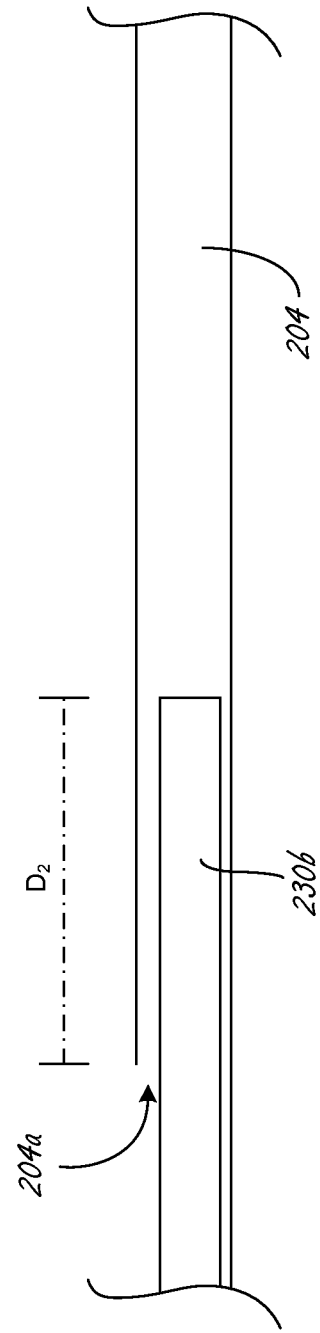

FIG. 4C is a cross-sectional view of the device 200 in a second configuration different than the first configuration. In particular, relative to the first configuration shown in FIG. 4A, the actuation assembly 210 (FIGS. 2 and 3) has been actuated to drive the rack element 230 away from the outflow port 204b (e.g., moving the rack element 230 at least partially out of the lumen 204). As a result, the engagement element 223 engages a second groove 232b that is different than the first groove 232a. FIG. 4D is an enlarged view of aspects of the device 200 in the second configuration. As illustrated, the distal end portion 230b still extends into the lumen 204 in the second configuration. The distal end portion 230b extends into the lumen 204 by a distance $D_2$, as measured from the inflow port 204a. In some embodiments, the distance $D_2$ is less than the distance $D_1$. Accordingly, the length of the lumen 204 that is occupied by the rack element 230 is decreased in the second configuration relative to the first configuration. Without being bound by theory, it is expected that, at any given pressure differential between the inflow port 204a and the outflow port 204b, reducing the length of the lumen 204 that is occupied by the rack element 230 (e.g., by moving from the first configuration to the second configuration) decreases the flow resistance through the lumen 204, and therefore increases the flow of fluid through the lumen 204. Moreover, in some embodiments, the distal end portion 230b of the rack element 230 may be completely removable from the lumen 204 upon repetitive actuation of the actuation assembly 210. Although the foregoing describes adjusting a fluid resistance through the lumen 204 using a linear motion of the rack element 230, the fluid resistance through the lumen 204 may alternatively be adjusted by using the actuation assembly 210 to constrict or expand a diameter of the lumen, thereby increasing or decreasing fluid resistance through the lumen 204.

FIGS. 5A-5D illustrate another embodiment of an adjustable flow glaucoma treatment device 500 ("device 500") configured in accordance with embodiments of the present technology. The device 500 can be similar in certain aspects to device 200. For example, referring to FIG. 5A, the device 500 can include a base 502 implantable into a portion of an eye (e.g., an anterior chamber) and having a lumen 204 extending therethrough. The device 500 can further include an actuation assembly 510 having a first actuation element 512 and a second actuation element 514. In some embodiments, the first actuation element 512 is generally similar to the first actuation element 212 (FIG. 2), and the second actuation element 514 is generally similar to the second actuation element 214 (FIG. 2). The device 500 can further include an arm 520, a rack element 530, and a locking mechanism 535. As described in detail above with reference to the device 200, the actuation assembly 510 can be actuated to move the rack element 530 into or out of the lumen 504 to change a flow resistance therethrough.

Figure 5A:
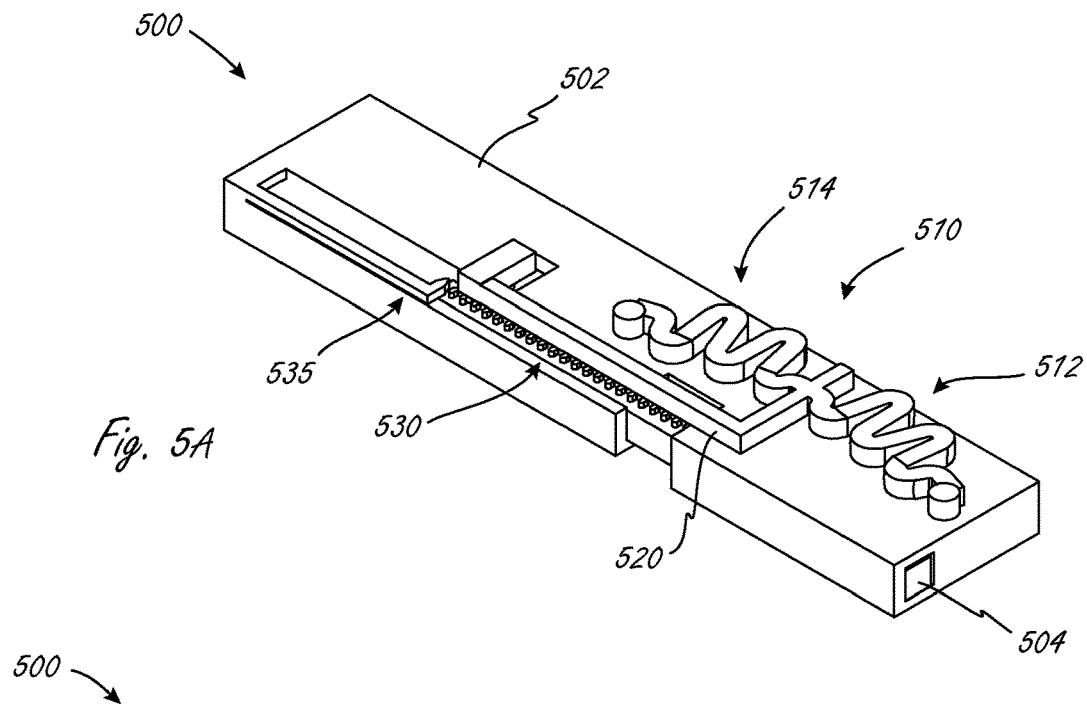
FIGS. 5A-5D illustrate an adjustable glaucoma treatment device configured in accordance with select embodiments of the present technology.
Figure 5B:
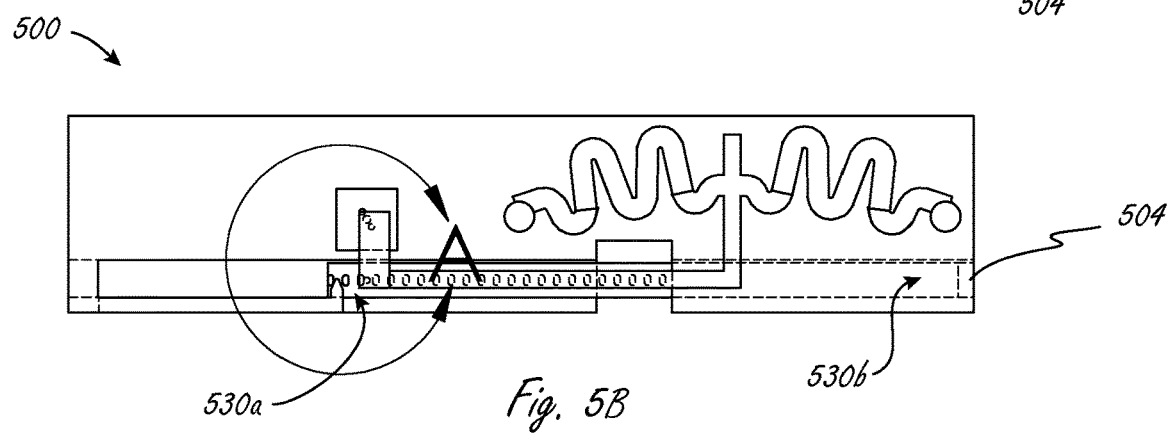
Figure 5C:
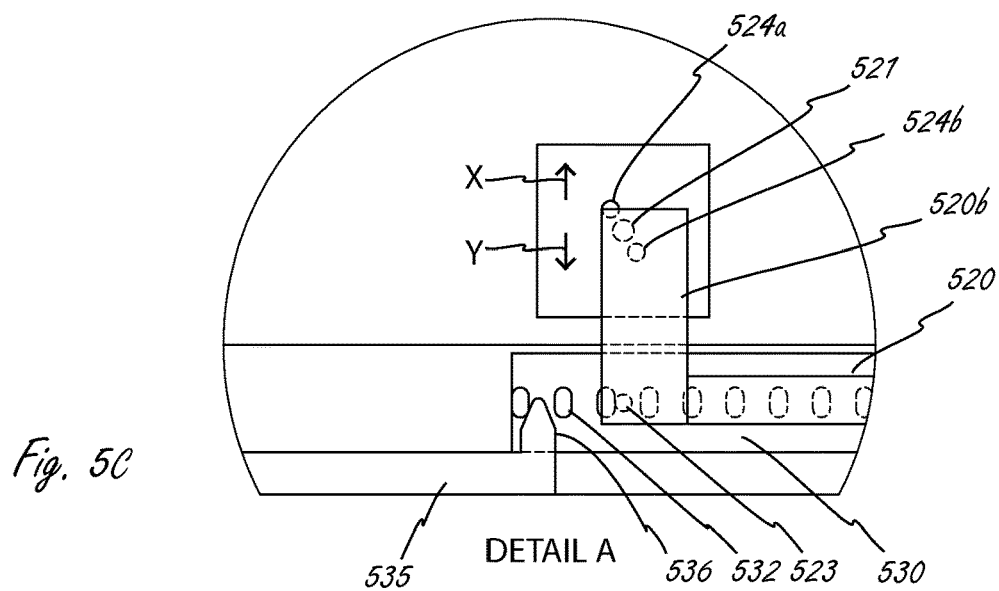

FIG. 5B is a front view of the device 500, and FIG. 5C is an enlarged view of the portion of the device 500 indicated in FIG. 5B. Referring to FIGS. 5B and 5C together, the rack element 530 includes a plurality of teeth or other protrusions 532 that define corresponding grooves therebetween. As described above with respect to the rack element 230, the rack element 530 can also be a sawtooth wire or other element that creates an engageable surface for releasably mating with the arm 520. The latching mechanism 535 can include a locking element 536 that can engage with the rack element 530 in a groove between two adjacent teeth 532. The device 500 further includes a first blocking element 524a and a second blocking element 524b. As described in greater detail below with reference to FIG. 5D, the first blocking element 524a and the second blocking element 524b restrain movement of the arm 520 to a predefined path.

The arm 520 includes a distal end portion 520b having a general "L" shape. The distal end portion 520b includes an engagement element 523 at or near the bend of the "L" that can engage with the rack element 530. The distal end portion 520b also includes a knob element 521. The knob element 521 can protrude from the distal end portion 520b towards the base 502. The knob element 521 is sized and shaped such that it can engage with, or otherwise contact, the first blocking element 524a and the second blocking element 524b. In the illustrated configuration, the first blocking element 524a restrains motion of the distal end portion 520b of the arm 520 in a first direction (indicated by arrow X) via engagement with the knob element 521. Likewise, the second blocking element 524b restrains motion of the distal end portion 520b of the arm 520 in a second direction (indicated by arrow Y) via engagement with the knob element 521. However, as described below with reference to FIG. 5D, actuation of the first actuation element 512 will move the knob element 521 out of contact with the first blocking element 524a, permitting the distal end portion 520b to move in the first direction X. Likewise, actuation of the second actuation element 514 will move the knob element 521 out of contact with the second blocking element 524b, permitting the distal end portion 520b to move in the second direction Y. However, when the device 500 is in the configuration illustrated in FIG. 5C, movement of the arm 520 is minimized in both the first direction X or the second direction Y at its distal end portion 520b and, as a result, the arm 520 remains engaged with the rack element 530. As will be apparent from the following description, and unlike the device 200 described above, the device 500 does not need channels cut into the arm 520 to facilitate disengagement of the arm 520 from the rack element 530.

Figure 5D:
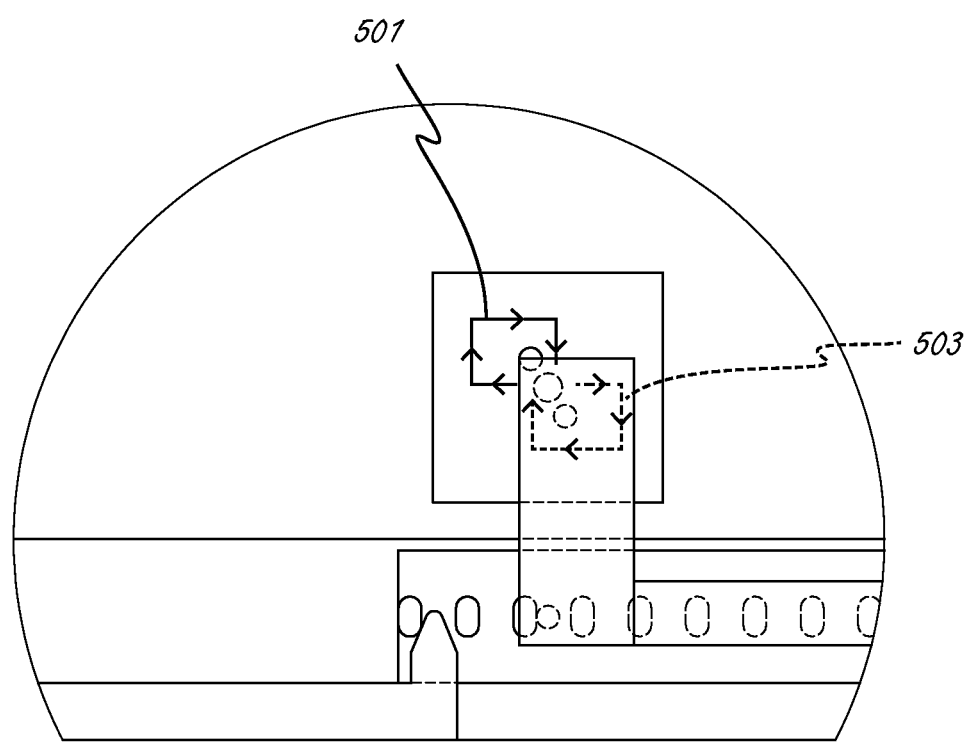

FIG. 5D illustrates a first path 501 (shown with solid arrows) and a second path 503 (shown with dashed arrows) that the arm 520 can move through during actuation of the actuation assembly 510. For example, with reference to FIGS. 5C and 5D together, upon initial actuation of the first actuation element 512, the distal end portion 520b of the arm 520 moves towards the locking mechanism 535. Because the arm 520 is engaged with the rack element 530 via the engagement element 523, movement of the distal end portion 520b towards the locking mechanism 535 also causes the rack element 530 to slide in the same direction (i.e., pulling the rack element 530 further out of the lumen 504, described in detail with respect to the device 200 in FIG. 4A-4D). As the distal end portion 520b moves towards the locking mechanism 535, the knob element 521 moves out of engagement with the first blocking element 524a. This permits the distal end portion 520b of the arm 520 to swing upward (e.g., as indicated by the arrows along the first path 501 of FIG. 5D) and disengage from the rack element 530. When the arm 520 is disengaged from the rack element 530, the locking mechanism 535 holds the rack element 530 in position. In embodiments in which the actuation assembly 510 exhibits a recoil effect, the distal end portion 520b of the arm can automatically move through the remainder of the first path 501 until the knob element 521 returns to the original position between the first blocking element 524a and the second blocking element 524b. In embodiments in which the actuation assembly 510 does not exhibit a recoil effect, the second actuation element 514 can then be actuated to drive the distal end portion 520b through the remainder of the first path 501 until the knob element 521 returns to the original position between the first blocking element 524a and the second blocking element 524b. When the knob element 521 returns to the original position, the engagement element 523 reengages the rack element 530, but at a different groove than it engaged with before moving through the first path 501. The net effect of the arm 520 moving through the first path 501 is the movement of the rack element 530 in a first direction (e.g., away from the lumen 504) that can decrease the flow resistance through the lumen 504.

The movement of the rack element 530, and therefore the change to the lumen 504, is reversible by moving the distal end portion 520b of the arm 520 through the second path 503 (FIG. 5D). Movement of the arm 520 through the second path 503 occurs in a similar manner to movement of the arm 520 through the first path 501. For example, upon initial actuation of the second actuation element 514, the distal end portion 520b of the arm 520 moves away from the locking mechanism 535. Because the arm 520 is engaged with the rack element 530 via the engagement element 523, movement of the distal end portion 520b away from the locking mechanism 535 also causes the rack element 530 to slide in the same direction (i.e., pushing the rack element 530 further into the lumen 504, described in detail with respect to the device 200 in FIG. 4A-4D). As the distal end portion 520b moves away from the locking mechanism 535, the knob element 521 moves out of engagement with the second blocking element 524b. This permits the distal end portion 520b of the arm 520 to swing downward (e.g., as indicated by the arrows along the second path 503 of FIG. 5D) and disengage from the rack element 530. When the arm 520 is disengaged from the rack element 530, the locking mechanism 535 holds the rack element 530 in position. In embodiments in which the actuation assembly 510 exhibits a recoil effect, the distal end portion 520b of the arm can automatically move through the remainder of the second path 503 until the knob element 521 returns to the original position between the first blocking element 524a and the second blocking element 524b. In embodiments in which the actuation assembly 510 does not exhibit a recoil effect, the first actuation element 512 can be then be actuated to drive the distal end portion 520b through the remainder of the second path 503 until the knob element 521 returns to the original position between the first blocking element 524a and the second blocking element 524b. When the knob element 521 returns to the original position, the engagement element 523 reengages the rack element 530, but at a different groove than it engaged with before moving through the second path 501. The net effect of the arm 520 moving through the second path 503 is the movement of the rack element 530 in a second direction (e.g., further into the lumen 204) that is generally opposite the first direction the rack element 530 moved when the arm 520 went through the first path 501. For example, movement of the arm 520 through the second path 503 can increase the flow resistance through the lumen 504.

Although the foregoing describes the rack element 530 moving from a first position to a second position via movement of the arm through the first path 501 and moving from the second position back to the first position via movement of the arm through the second path 503, the device 500 is capable of moving between other configurations. For example, the arm 520 can be driven through the first path 501 multiple times without driving the arm 520 through the second path 503. Each time the arm 520 moves through the first path 501, the rack element 530 slides further in the first direction (e.g., further out of the lumen 204). Likewise, the arm 520 can be driven through the second path 503 without first moving the arm 520 through the first path 501 to cause the rack element 530 to move in the second direction opposite the first direction (e.g., further into the lumen 204). Accordingly, the rack element 530 can be selectively moved in opposite directions by selectively actuating the actuation assembly 510 to move the arm through the first path 501 and/or the second path 503, respectively.

At least some aspects of the devices described herein (e.g., the device 200 or device 500) can be formed using a photolithographic process. For example, a photomask having a desired geometric pattern (e.g., having the channel 240, the frame 206, etc.) can be placed over a photosensitive substrate. Upon application of light, the geometric pattern is imprinted on the substrate, forming the base (e.g., the base 202). In some embodiments, aspects of the device 200 or 500 (e.g., the base) can be formed as stacked sheets of material (e.g., laminate) to increase the structural integrity of the component (e.g., the base).

In some embodiments, the devices described herein (e.g., device 200 or 500) can be manufactured using a deposition process using polymers and/or metal. For example, in some embodiments a vapor deposition process can deposit process metals such as palladium, rhodium, nickel-titanium, and/or nickel-cobalt alloys onto a substrate. The process metals can be deposited in relatively thin layers (e.g., about 5 micron) that form the various structures of the device. In some embodiments, a sacrificial material (e.g., copper) can be deposited as a placeholder during deposition and can subsequently and selectively be etched away to form the various void spaces within the device (e.g., the lumen) and/or between components (e.g., between the rack element and the channel). One expected advantage of relying on a deposition fabrication process is that discrete portions of the device (including moveable components such as the rack element) can be manufactured simultaneously in an assembled configuration. This is expected to reduce the time required to assemble the device compared to methods that fabricate various components of the device separately.

In some embodiments, some or all of the device, such as the actuation assembly 210, can be laser cut from a piece (e.g., sheet, strip, tube, etc.) of nitinol or other suitable material. The first actuation element 212 and the second actuation element 214 can be shape set such that the first actuation element 212 and the second actuation element 214 have a desired configuration or shape (e.g., length) when heated above a certain temperature (e.g., a temperature that is greater than body temperature). Once shape set, and at a temperature below the transition temperature, the first actuation element 212 and/or the second actuation element 214 can be compressed or otherwise stressed inwards (or alternatively stretched in embodiments operating under tension) and fixed to the anchoring elements 206a and 206b (e.g., via the notches 207a, 207b). Optionally, one of the actuation elements 212, 214 can be heated to assume the shape memory state before securing the actuation elements 212, 214 to the anchoring elements 206a, 206b to bias the actuation assembly 210.

Figure 6A:
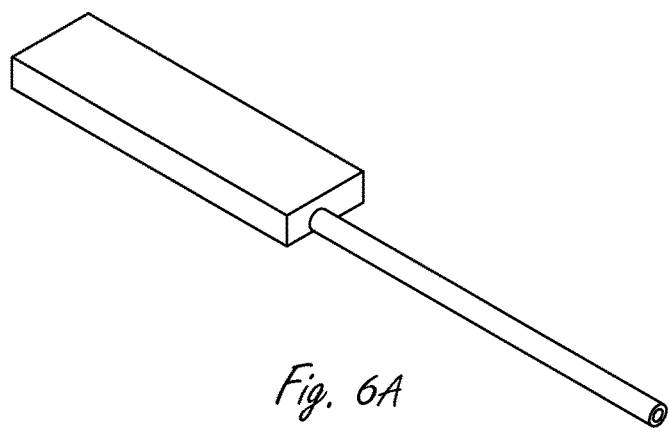
FIGS. 6A and 6B illustrate an adjustable glaucoma treatment device configured in accordance with select embodiments of the present technology.
Figure 6B:
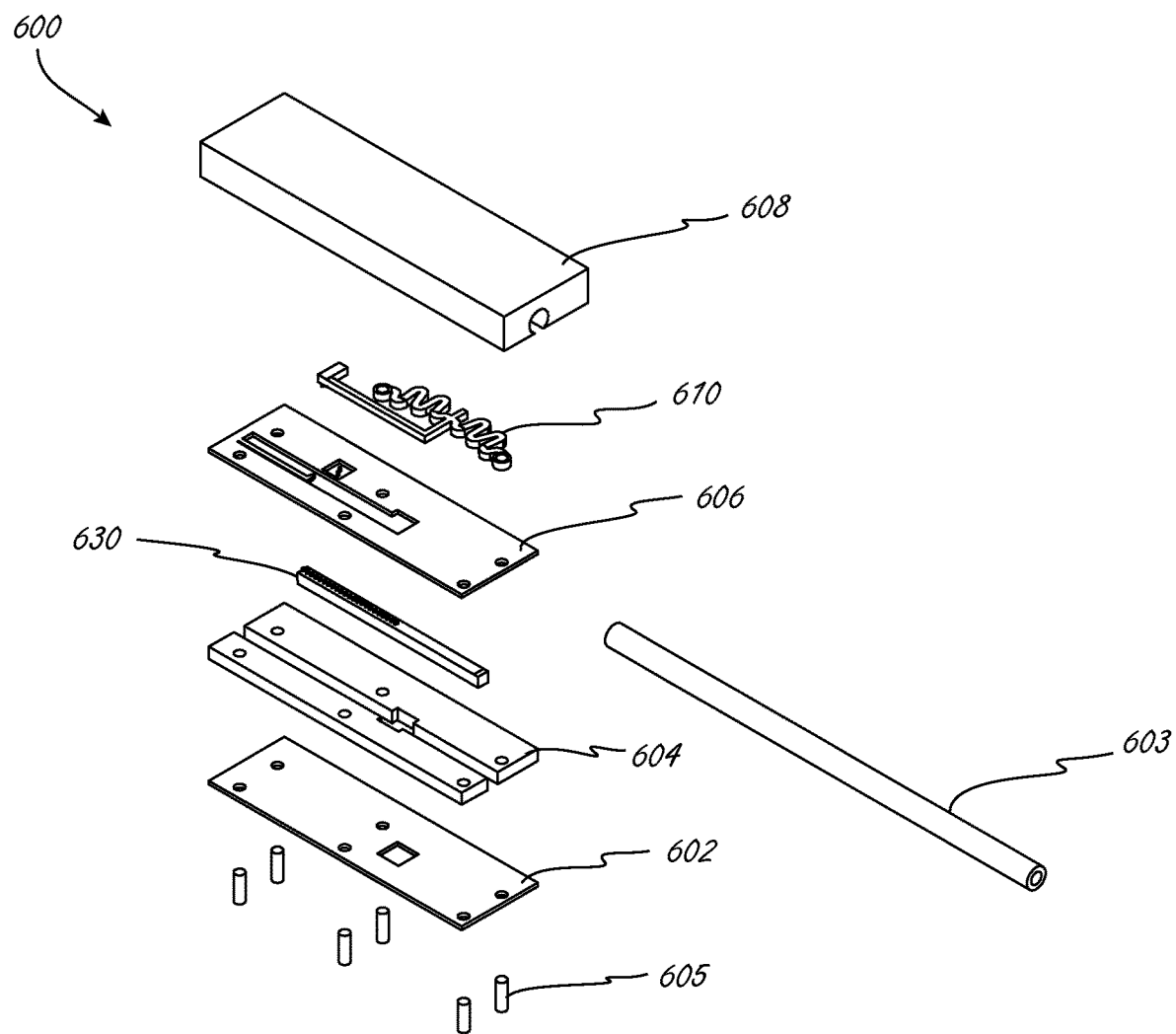

In some embodiments, individual components of the devices described herein (e.g., device 200 or device 500) are laser cut from a piece of material (e.g., nitinol) and then secured together using pins, welding, or other fastening mechanisms. FIG. 6A, for example, illustrates a device 600 manufactured through such process. FIG. 6B shows the device 600 in an exploded view, illustrating the various individually cut components before being assembled together. Referring to FIG. 6B, the individual components include a first base portion 602, a second base portion 604 that defines a channel, a rack element 630 positionable within the channel in the second base portion 604, a third base portion 606, an actuation assembly 610, and a cover 608. Each of the foregoing components can be secured together using a plurality of pins 605 or other suitable fastening mechanism(s) to form the assembled device 600 (FIG. 6A). The device 600 can also include an individually fabricated drainage element 603 for routing fluid to a desired drainage location.

As one of skill in the art will appreciate, the present technology is not limited to the embodiments explicitly described above. Rather, certain features described above can be incorporated into other suitable glaucoma devices or shunts, such as those described in U.S. patent application Ser. No. 17/175,332, U.S. Patent App. Publication No. 2020/0229982, and International Patent Application Nos.

PCT/US20/55144, PCT/US20/55141, and PCT/US21/14774, the disclosures of which are incorporated herein by reference in their entireties. For example, in some embodiments, the present technology provides an adjustable flow shunt having a drainage element and an actuation assembly, but the rack element and associated features (e.g., the rack element 230 and/or the arm 220 described in FIGS. 2 and 3) are omitted. In other embodiments, the present technology provides an adjustable flow shunt having the ratchet mechanism, but not the surface 208.

Figure 7A:
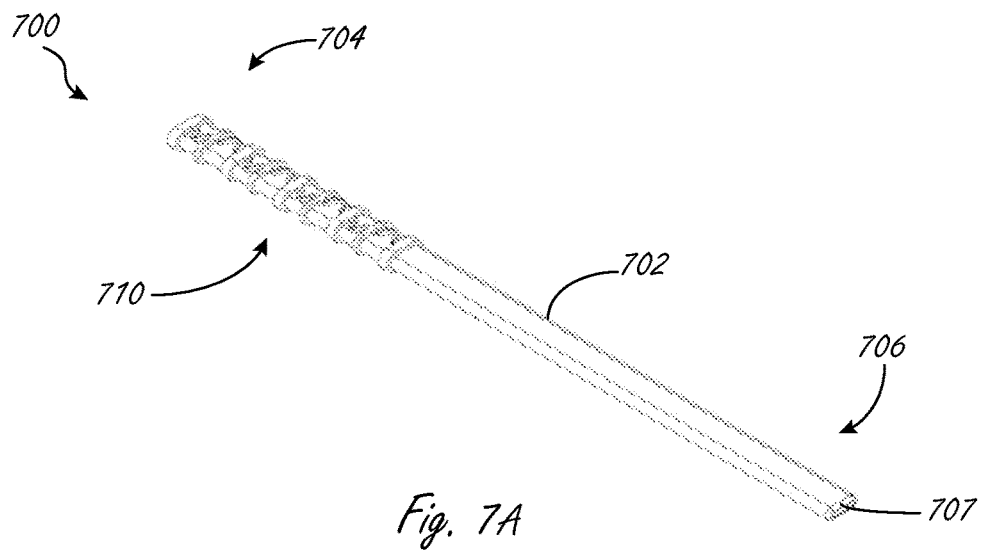
FIGS. 7A-7C illustrate another adjustable glaucoma treatment device configured in accordance with select embodiments of the present technology.
Figure 7B:
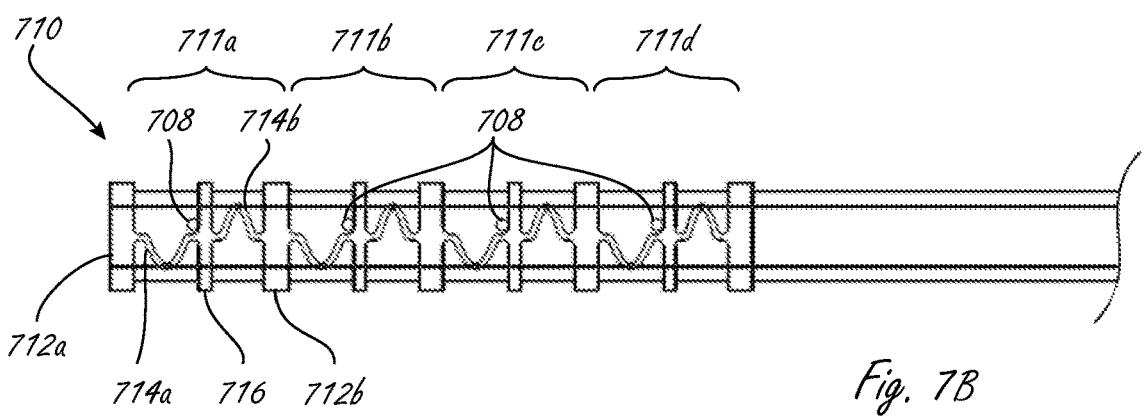
Figure 7C:
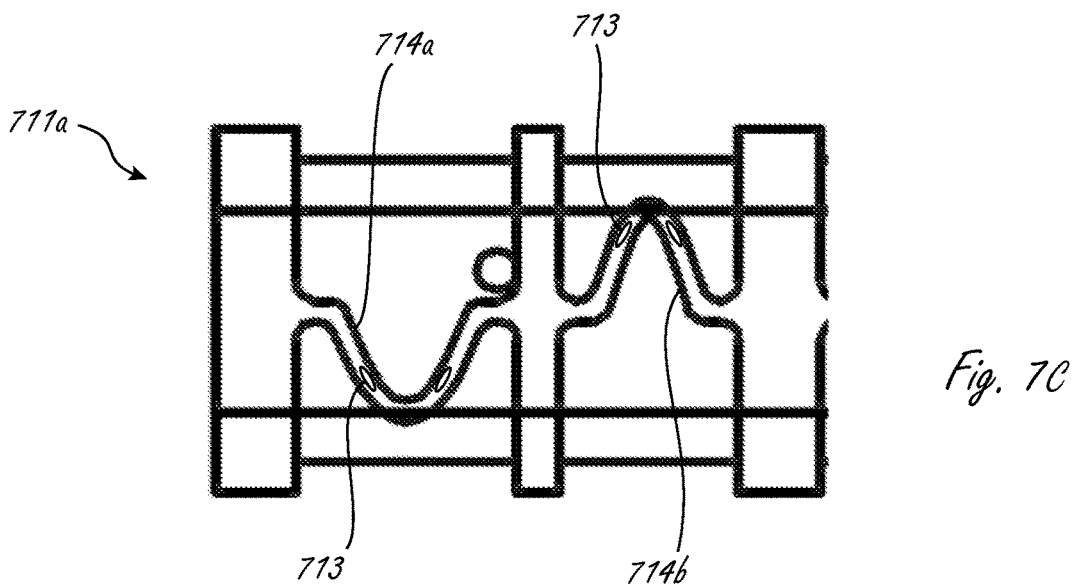

FIGS. 7A-7C, for example, illustrate an embodiment of a device 700 configured in accordance with select embodiments of the present technology in which the rack element and associated features are omitted. Referring to FIG. 7A, the device 700 includes a drainage element 702 (e.g., a tube or other suitable feature) having a first end portion 704 and a second end portion 706. The drainage element 702 can include a plurality of first ports or apertures 708 (FIG. 7B) at or adjacent the first end portion 704 and a second port 707 at or adjacent the second end portion 706. A lumen can extend through the drainage element 702 to fluidly connect the plurality of first ports 708 and the second port 707.

The device 700 can include an actuation assembly 710 positioned at the first end portion 704 of the drainage element 702. When the device 700 is implanted in an eye, the first end portion 704 can reside within an anterior chamber and the second end portion 706 can reside in a desired outflow location (e.g., a bleb space). In such embodiments, the actuation assembly 710 is located within the anterior chamber. In other embodiments, the first end portion 704 can reside within the desired outflow location and the second end portion 706 can reside within the anterior chamber. In such embodiments, the actuation assembly 710 is positioned outside of the anterior chamber (e.g., in the bleb space). Regardless of the orientation of the device 700, the device 700 is configured to drain aqueous from the anterior chamber when the device 700 is implanted in the eye. The device 700 may optionally have additional features that help secure the device 700 in place when implanted in the eye. For example, the device 700 can include arms, anchors, plates, or other suitable features configured to secure the device 700 to native tissue.

Referring to FIG. 7B, the actuation assembly 710 comprises a plurality of flow control mechanisms 711a-d arranged in series along the length of the drainage element 702. Each flow control mechanism 711a-d can interface with a corresponding first port 708, and each flow control mechanism 711a-d can be individually actuatable. The individual flow control mechanisms 711a-d further include a moveable gating element 416, a first actuation element (e.g., first actuation element 714b) extending between a first anchor (e.g., the first anchor 712a) and the gating element 416, and a second actuation element (e.g., second actuation element 714b) extending between a second anchor (e.g., the second anchor 712b) and the gating element 416. Each gating element 416 is configured to interface with (e.g., at least partially block) a corresponding first port 708.

The actuation elements 714a, 714b can operate in a similar manner as that of actuation elements 212 and 214 of device 200 described above with reference to FIG. 2. However, rather than moving an arm to engage and disengage a rack element, the actuation elements 714a, 714b shuttle the gating element 416 back and forth to open (or partially open) or close (or partially close) the corresponding port 708. Accordingly, the actuation elements 714a, 714b can be selectively modulated (e.g., targeted with energy from an energy source external to a patient) to change a flow characteristic of the device 700.

As described above in Section B and with respect to actuation elements 212 and 214 (FIGS. 2 and 3), the actuation elements 714a, 714b can comprise a shape memory material configured to change shape upon application of energy. For example, in some embodiments the actuation elements 714 are composed of nitinol. In such embodiments, applying energy (e.g., heat, light, etc.) to the actuation elements 714 causes the energized actuation element to transition from a first state (e.g., a martensitic or intermediate state) to a second state (e.g., an intermediate or an austenitic state). The transition from the first state to the second state can induce a dimensional change in the actuation element. In some embodiments, the dimensional change is an expansion. In other embodiments, the dimensional change is a reduction (e.g., compression). The energy may be applied from an energy source positioned external to the eye (e.g., a laser), which can enable a user to remotely adjust the device.

Referring to FIG. 7C, the actuation elements (e.g., the first actuation element 714a and the second actuation element 714b) can include one or more targets 713. As described above with respect to the targets 213b-e and 215b-e on device 200 (FIG. 2), the targets 713 can be recesses, wells, channels, divots, or other features configured to promote penetration of energy into the corresponding actuation element to thereby provide a relatively more even heating of the full thickness of the actuation element. For example, in the illustrated embodiment the targets 713 are cylindrical recesses that extend at least partially into the first actuation element 714a and the second actuation element 714b. Applying energy to one of the targets 713 is expected to provide more even heating through the full thickness of the actuation element adjacent the heated target 713 (as opposed to just heating the surface of the actuation element). Without being bound by theory, the relatively even application of energy throughout the full thickness of various regions of the actuation elements 714a, 714b is expected to increase the reproducibility and consistency of motion of the actuation elements 714a, 714b, which in turn is expected to increase the precision of adjustments to the flow through the device 700.

As one skilled in the art will appreciate, the devices described herein can include additional or fewer components than explicitly described without deviating from the scope of the present technology. Moreover, the devices described herein can be composed of any suitable material(s) for implantation into a human eye. In some embodiments, the materials can be selected based at least in part on one or more desired properties of the device. As a non-limiting example, and as one skilled in the art will appreciate, the devices can be treated and/or composed of a material to prevent biofilm growth on one or more surfaces of the device. Accordingly, in some embodiments, the devices described herein can include a coating or material configured to reduce biofilm formation. Furthermore, in some embodiments, at least some components of the devices described herein can be treated with beta radiation (or other suitable radiation or substances) to prevent and/or reduce the growth of biofilm on the components. The components may also be treated with beta radiation or with other suitable techniques to reduce and/or clear biofilm formations already formed on the devices. Accordingly, the components can be treated before implantation of the device into a human eye, after implantation of the device into the human eye, or both before and after implantation of the device into the human eye.

EXAMPLES

Several aspects of the present technology are set forth in the following examples:

1. A device for treating glaucoma, the device comprising:
   a drainage element at least partially defining a lumen configured to drain aqueous from an anterior chamber of an eye;
   a flow control element moveable between at least a first position and a second position and configured to change a flow resistance through the device;
   an actuation assembly including—
      an actuation element configured to at least partially change shape and/or size in response to energy, and
      an arm extending from the actuation element and configured to releasably engage the flow control element,
      wherein, when the arm engages a first region of the flow control element, actuation of the actuation element causes the arm to move the flow control element between the first position and the second position to change the flow resistance through the device; and
   a locking mechanism configured to at least partially reduce movement of the flow control element when the arm is disengaged from the flow control element.

2. The device of example 1 wherein the flow control element comprises a slidable rack element.

3. The device of example 2 wherein the slidable rack element has a first groove and a second groove, and wherein the arm has an engagement element configured to releasably engage the slidable rack element at the first groove and/or second groove.

4. The device of example 3 wherein the first region of the flow control element is the first groove, and wherein after the flow control element is moved from the first position to the second position, the engagement element is configured to disengage from the first groove and engage with the second groove.

5. The device of example 4 wherein the locking mechanism engages with the flow control element to at least partially reduce movement of the flow control element after the engagement element disengages from the first groove and before the engagement element engages with the second groove.

6. The device of any of examples 3-5 wherein the slidable rack element has a third groove and a fourth groove, and wherein the locking mechanism includes a locking element configured to engage the third groove when the flow control element is in the first position and configured to engage the fourth groove when the flow control element is in the second position.

7. The device of any of examples 1-7 wherein the locking mechanism is configured to prevent movement of the flow control element when the arm is disengaged from the flow control element via a friction fit with the arm.

8. The device of any of examples 1-8 wherein the actuation element is a first actuation element, the actuation assembly further comprising a second actuation element connected to the arm and configured to at least partially change shape and/or size in response to energy.

9. The device of example 8 wherein, when the flow control element is in the second position, actuation of the second actuation element causes the arm to move the flow control element from the second position to the first position.

10. The device of example 9 wherein the first actuation element and the second actuation comprise a shape memory material.

11. The device of example 10 wherein the first actuation element has a first bend region, and wherein application of energy to the first bend region causes the first bend region to expand.

12. The device of example 10 or 11 wherein the second actuation element has a second bend region, and wherein application of energy to the second bend region causes the second bend region to expand.

13. The device of example 12 wherein actuation of the first actuation element causes the second actuation element to compress at the second bend region, and wherein actuation of the second actuation element causes the first actuation element to compress at the first bend region.

14. The device of any of examples 1-13 wherein the flow control element is moveable through three or more positions, wherein each of the three or more positions is associated with a unique flow resistance through the device.

15. The device of any of examples 1-14 wherein, when the device is implanted in a human eye, the actuation element is configured to receive energy from an energy source positioned external to the eye.

16. The device of example 15 wherein the energy source is a laser.

17. The device of any of examples 1-16 wherein the device is configured such that changing a flow resistance through the device when the device is implanted in a human eye changes the drainage rate of aqueous from the anterior chamber of the eye.

18. The device of any of examples 1-17 wherein the flow control element is configured to change a diameter of the lumen as it moves between the first position and the second position.

19. A device for controlling fluid flow between a first region and a second region, the device comprising:
   a lumen configured to drain fluid from the first region toward the second region;
   a ratchet mechanism configured to alter the flow of fluid through the lumen, wherein the ratchet mechanism includes—
      a rack element moveable between a first position in which the lumen has a first shape and a second position in which the lumen has a second shape different than the first shape,
      an engagement element configured to releasably engage the rack element, and
      an actuation assembly connected to the engagement element and configured to move the rack element between the first position and the second position.

20. The device of example 19, further comprising an arm connected to the actuation assembly, wherein the arm includes the engagement element and is configured to drive the rack element from the first position to and/or toward the second position upon actuation of the actuation assembly.

21. The device of example 19 or 20 wherein the rack element includes a plurality of teeth and a plurality of grooves, and wherein the engagement element is configured to engage the rack element in one of the plurality of grooves.

22. The device of example 20 or 21 wherein, after the rack element is moved from the first position to and/or toward the second position, the engagement element is configured to disengage from a first groove on the rack element and engage with a second groove on the rack element.

23. The device of any of examples 19-22 wherein the actuation assembly includes a first actuation element configured to move the rack element in a first direction and a second actuation element configured to move the rack element in a second direction generally opposite the first direction.

24. The device of example 23 wherein the first actuation element is configured to move the rack element from the first position to the second position and the second actuation element is configured to move the rack element from the second position to the first position.

25. The device of example 23 or 24 wherein the first actuation element and the second actuation element are configured to change dimension upon application of energy.

26. The device of any of examples 23-25 wherein the first actuation element and the second actuation element are composed of nitinol.

27. The device of any of examples 19-26 wherein the rack element directly engages the lumen to change the lumen from the first shape to the second shape as the rack element moves from the first position to and/or toward the second position.

28. The device of any of examples 19-26 wherein the rack element indirectly engages the lumen to change the lumen from the first shape to the second shape as the rack element moves from the first position to and/or toward the second position.

29. The device of example 28, further comprising a flow control element operably connected to the rack element, and wherein the flow control element directly engages the lumen to change the lumen from the first shape to the second shape.

30. The device of any of examples 19-29, further comprising a locking mechanism configured to hold the rack element in position when the arm element disengages from the rack element.

31. The device of any of examples 19-30 wherein the first body region is an anterior chamber of a human eye, and wherein the device is configured such that changing the shape characteristic of the lumen when the device is implanted in the eye changes the drainage rate of aqueous from the anterior chamber of the eye.

32. The device of any of examples 19-31 wherein the rack element is configured to change a diameter of lumen as it moves between the first position and the second position.

33. A device for controlling fluid flow between a first region and a second region, the device comprising:
   a drainage element at least partially defining a lumen configured to drain fluid from the first region to the second region;
   a flow control element moveable between at least a first position and a second position and configured to change a flow resistance through the device;
   an actuation assembly including—
      an actuation element configured to at least partially change shape and/or size in response to energy, and
      an arm extending from the actuation element and configured to releasably engage the flow control element,
      wherein, when the arm engages a first region of the flow control element, actuation of the actuation element causes the arm to move the flow control element between the first position and the second position to change the flow resistance through the device; and
   a locking mechanism configured to at least partially reduce movement of the flow control element when the arm is disengaged from the flow control element.

34. The device of example 33 wherein the flow control element comprises a slidable rack element.

35. The device of example 34 wherein the slidable rack element has a first groove and a second groove, and wherein the arm has an engagement element configured to releasably engage the slidable rack element at the first groove and/or second groove.

36. The device of example 35 wherein the first region of the flow control element is the first groove, and wherein after the flow control element is moved from the first position to the second position, the engagement element is configured to disengage from the first groove and engage with the second groove.

37. The device of example 36 wherein the locking mechanism engages with the flow control element to at least partially reduce movement of the flow control element after the engagement element disengages from the first groove and before the engagement element engages with the second groove.

38. The device of any of examples 35-37 wherein the slidable rack element has a third groove and a fourth groove, and wherein the locking mechanism includes a locking element configured to engage the third groove when the flow control element is in the first position and configured to engage the fourth groove when the flow control element is in the second position.

39. The device of any of examples 33-39 wherein the locking mechanism is configured to prevent movement of the flow control element when the arm is disengaged from the flow control element.

40. The device of any of examples 33-40 wherein the actuation element is a first actuation element, the actuation assembly further comprising a second actuation element connected to the arm and configured to at least partially change shape and/or size in response to energy.

41. The device of example 40 wherein, when the flow control element is in the second position, actuation of the second actuation element causes the arm to move the flow control element from the second position to the first position.

42. The device of example 41 wherein the first actuation element and the second actuation comprise a shape memory material.

43. The device of example 42 wherein the first actuation element has a first bend region, and wherein application of energy to the first bend region causes the first bend region to expand.

44. The device of example 42 or 43 wherein the second actuation element has a second bend region, and wherein application of energy to the second bend region causes the second bend region to expand.

45. The device of example 44 wherein actuation of the first actuation element causes the second actuation element to compress at the second bend region, and wherein actuation of the second actuation element causes the first actuation element to compress at the first bend region.

46. The device of any of examples 33-45 wherein the flow control element is moveable through three or more positions, wherein each of the three or more positions is associated with a different flow resistance through the device.

47. The device of any of examples 33-46 wherein the device is configured such that changing the flow resistance through the device when the device is implanted changes the drainage rate of fluid from the first region.

48. The device of any of examples 33-47 wherein the first region is an anterior chamber of an eye.

49. The device of any of examples 33-48 wherein the flow control element is configured to change a diameter of the lumen as it moves between the first position and the second position 50. An implantable medical device for draining fluid from a first body region to a second body region, the device comprising:
   a drainage element having a lumen extending therethrough and configured to fluidly connect the first body region and the second body region; and
   a flow control element moveable through a plurality of discrete positions, wherein each discrete position is associated with a relative fluid resistance through the device, and wherein the flow control element is selectively moveable between the plurality of discrete positions.

51. The device of example 50 further comprising a ratchet mechanism configured to move the flow control element through the plurality of discrete positions.

52. The device of examples 50 or 51, further comprising an actuation assembly configured to move the flow control element through the plurality of discrete positions, wherein the actuation assembly includes at least one actuation element and a ratchet mechanism.

53. The device of example 52 wherein the implantable medical device is a glaucoma shunt, and wherein the first body region is an anterior chamber of an eye.

54. The device of any of examples 50-53 wherein the flow control element is configured to change a dimeter of the lumen as it moves between the plurality of discrete positions.

55. An implantable medical device for draining fluid from a first body region to a second body region, the device comprising:
   a drainage element configured to fluidly connect the first body region and the second body region when the device is implanted in a patient; and
   an actuation assembly configured to adjust the flow of fluid through the drainage element, the actuation assembly including a shape-memory actuation element moveable between a pre-actuated configuration and an actuated configuration,
   wherein the device is configured such that—
   when actuated, the shape-memory actuation element moves from the pre-actuated configuration to and/toward the actuated configuration to adjust a fluid resistance through the device, and
   following actuation (a) the shape-memory actuation element recoils toward the pre-actuated configuration, and (b) the adjusted fluid resistance is maintained as the shape-memory actuation element recoils toward the pre-actuated configuration.

56. The device of example 55, further comprising:
   a flow control element operably coupled to the shape-memory actuation element and configured to control the fluid resistance through the device,
   wherein the flow control element is configured to move from a first position to and/or toward a second position when the shape-memory actuation element moves from the pre-actuated configuration to and/or toward the actuated configuration, and
   wherein the flow control element is configured to be retained at and/or proximate the second position when the shape-memory actuation element recoils toward the pre-actuated configuration.

57. The device of example 56, further comprising a ratchet configured to retain the flow control element at and/or proximate the second position.

58. The device of example 55 wherein the shape-memory actuation element is configured to move from the pre-actuated configuration to and/or toward the actuation configuration when heated above a transition temperature, and wherein the shape-memory actuation element is configured to recoil toward the pre-actuated when cooled below the transition temperature.

59. The device of any of examples 55-58, further comprising an elastic member configured to drive the recoil of the shape-memory element toward the pre-actuated configuration.

60. The device of any of examples 55-59 wherein the shape-memory actuation element is configured to be repeatedly transitioned between the pre-actuated configuration and the actuated configuration to further adjust the fluid resistance through the device.

61. A method of controlling the flow of fluid from a first body region to a second body region using an adjustable shunting device, the method comprising:
   heating a shape-memory actuation element of the adjustable shunting device above a transition temperature to move the shape-memory actuation element from a first configuration to and/or toward a second configuration, wherein moving the shape-memory actuation element from the first configuration to and/or toward the second configuration adjusts a fluid resistance through the adjustable shunting device;
   after heating the shape-memory actuation element, recoiling the shape-memory actuation element toward the first configuration as the shape-memory actuation element cools below the transition temperature; and
   maintaining the adjusted fluid resistance as the shape-memory actuation recoils toward the first configuration.

62. The method of example 61 wherein the adjustable shunting device includes a flow control element configured to control the fluid resistance through the device, and wherein—
   moving the shape-memory actuation element from the first configuration to and/or toward the second configuration moves the flow control element from a first position to/and or toward a second position; and
   maintaining the adjusted fluid resistance includes retaining the flow control element at and/or proximate the second position as the shape-memory actuation element recoils toward the first configuration.

63. The method of example 62 wherein retaining the flow control element at and/or proximate the second position includes mechanically retaining the flow control element.

64. The method of example 61 wherein the adjusted fluid resistance is a first adjusted fluid resistance, the method further comprising:
   after maintaining the first adjust fluid resistance, reheating the shape-memory actuation element above the transition temperature to move the shape-memory actuation element to and/or toward the second configuration to further adjust the fluid resistance to a second adjusted fluid resistance; and
   maintaining the second adjusted fluid resistance as the shape-memory actuation element cools below the transition temperature and recoils toward the first configuration.

65. The method of any of examples 61-64 wherein recoiling the shape-memory actuation element toward the first configuration includes biasing the shape-memory actuation element toward the first configuration using an elastic element.

66. An implantable medical device for draining fluid from a first body region to a second body region, the device comprising:
   a fluid resistor;
   an actuation element transitionable between a plurality of geometries; and
   a ratchet operably coupled to the actuation element, wherein the ratchet is configured to induce a discrete change in a resistance created by the fluid resistor in response to the actuation element transitioning between geometries.

67. An implantable device for shunting fluid within a patient, the device comprising:
   a drainage element having a lumen extending therethrough;
   a flow control element moveable between at least a first position and a second position and configured to change a flow resistance through the device; and
   a first actuation element operably coupled to the flow control element, wherein the first actuation element includes a first target feature for receiving energy from an energy source positioned external to the patient; and
   a second actuation element operably coupled to the flow control element, wherein the second actuation element includes a second target feature for receiving energy from the energy source positioned external to the patient.

68. The device of example 67 wherein the flow control element is configured to move from the first position toward the second position when energy is applied to the first target feature, and wherein the flow control element is configured to move from the second position toward the first position when energy is applied to the second target feature.

69. The device of example 67 wherein the first actuation element includes a first bend region and the second actuation element includes a second bend region, and wherein the first target feature is positioned at the first bend region and the second target feature is position at the second bend region.

70. The device of example 69 wherein the first target feature is configured such that energy received at the first actuation element preferentially heats the first bend region, and wherein the second target feature is configured such that energy received at the second actuation element preferentially heats the second bend region.

71. The device of any of examples 67-70 wherein the first actuation element includes a plurality of first target features and the second actuation element includes a plurality of second target features.

72. The device of example 71 wherein—
   the first actuation element includes a plurality of first bend regions, and wherein individual first bend regions of the plurality of first bend regions have a corresponding first target feature, and
   the second actuation element includes a plurality of second bend regions, and wherein individual second bend regions of the plurality of second bend regions have a corresponding second target feature.

73. The device of example 72 wherein each of the plurality of first target features can be individually energized to selectively actuate the corresponding first bend region, and wherein each of the plurality of second target features can be individually energized to selectively actuate the corresponding second bend region.

74. The device of example 73 wherein the flow control element is moveable to a plurality of discrete positions between the first position and the second position by selectively actuating individual first bend regions and/or second bend regions.

75. The device of any of examples 67-74 wherein the first target feature is a first recess extending at least partially into the first actuation element and configured to allow energy to penetrate the first actuation element, and wherein the second target feature is a second recess extending at least partially into the second actuation element and configured to allow energy to penetrate the second actuation element.

76. The device of any of examples 67-74 wherein the first target feature is a first zone on the first actuation element having a higher absorption rate than regions of the first actuation element surrounding the first zone, and wherein the second target feature is a second zone on the second actuation element having a higher absorption rate than regions of the second actuation element surrounding the second zone.

77. The device of example 76 wherein the first zone and the second zone include an absorptive coating.

78. The device of example 76 wherein the first zone and the second zone are oxidized.

79. The device of any of examples 67-74 wherein the first target feature is proximate a first reflective surface configured to reflect energy directly received from the energy source positioned external to the patient, and wherein the second target feature is proximate a second reflective surface configured to reflect energy directly received from the energy source positioned external to the patient.

80. The device of example 79 wherein energy received at the first target feature directly heats the first target feature and indirectly heats at least a portion of the first reflective surface, and wherein energy received at the second target feature directly heats the second target feature and indirectly heats at least a portion of the second reflective surface.

81. The device of any of examples 67-80 wherein the implantable device is a glaucoma shunt configured to drain aqueous from an anterior chamber of an eye of the patient.

82. An implantable device for shunting fluid within a patient, the device comprising:
   a fluid flow path configured to drain fluid from a first location within the patient having a first pressure to a second location within the patient having a second pressure less than the first pressure;
   a flow control element moveable between at least a first position and a second position and configured to change a flow resistance through the fluid flow path; and
   an actuation assembly including an actuation element operably coupled to the flow control element, wherein the actuation element includes at least one target feature for receiving energy from an energy source positioned external to the patient.

83. The device of example 82 wherein the flow control element is configured to move from the first position toward the second position when energy is applied to the target feature.

84. The device of example 82 wherein the actuation element includes a bend region, and wherein the target feature is positioned at the bend region.

85. The device of example 84 wherein the target feature is configured such that energy received at the actuation element preferentially heats the bend region to cause a shape change at the bend region.

86. The device of any of examples 82-85 wherein the actuation element includes a plurality of target features.

87. The device of example 86 wherein the actuation element includes a plurality of bend regions, and wherein individual bend regions of the plurality of bend regions have a corresponding target feature.

88. The device of example 87 wherein each of the plurality of target features can be individually energized to selectively actuate the corresponding bend region.

89. The device of example 88 wherein the flow control element is moveable to a plurality of discrete positions between the first position and the second position by selectively actuating individual bend regions.

90. The device of any of examples 82-89 wherein the target feature is a recess extending at least partially into the actuation element and configured to allow energy to penetrate the actuation element.

91. The device of any of examples 76-83 wherein the target feature is a zone on the actuation element having a higher absorption rate than regions of the actuation element surrounding the zone.

92. The device of example 91 wherein the zone includes an absorptive coating.

93. The device of example 91 wherein the zone is oxidized.

94. The device of any of examples 82-93 wherein the implantable device is a glaucoma shunt configured to drain aqueous from an anterior chamber of an eye of the patient.

95. An implantable device for shunting fluid within a patient, the device comprising:
 a drainage element having a lumen extending therethrough; and
 an actuation element operably coupled to the drainage element and configured to change a flow resistance through the device when actuated, wherein the actuation assembly includes at least one target feature for receiving energy from an energy source positioned external to the patient.

96. The device of example 95 wherein the actuation element includes a bend region, and wherein the target feature is positioned at the bend region.

97. The device of example 96 wherein the target feature is configured such that energy received at the actuation element preferentially heats the bend region to cause a shape change at the bend region.

98. The device of any of examples 95-97 wherein the actuation element includes a plurality of target features.

99. The device of example 98 wherein the actuation element includes a plurality of bend regions, and wherein individual bend regions of the plurality of bend regions have a corresponding target feature.

100. The device of example 99 wherein each of the plurality of target features can be individually energized to selectively actuate the corresponding bend region.

101. The device of any of examples 95-100 wherein the target feature is a recess extending at least partially into the actuation element and configured to allow energy to penetrate the actuation element.

102. The device of any of examples 95-100 wherein the target feature is a zone on the actuation element having a higher absorption rate than regions of the actuation element surrounding the zone.

103. The device of example 102 wherein the zone includes an absorptive coating.

104. The device of example 102 wherein the zone is oxidized.

105. The device of any of examples 95-104 wherein the implantable device is a glaucoma shunt configured to drain aqueous from an anterior chamber of an eye of the patient.

106. A method of shunting fluid using an adjustable flow shunt implanted in a patient and having an actuation element, the method comprising:
 applying energy to a first region of the actuation element, the first region including a target feature for receiving the applied energy; and
 inducing, via the applied energy, a geometry change in the actuation element at the first region to change the flow resistance through the adjustable flow shunt.

107. The method of example 106 wherein applying energy to the first region comprises applying energy to the first region using an energy source positioned external to the patient.

108. The method of example 106 or 107 wherein the target feature increases the penetration of energy into the actuation element at the first region relative to a second region adjacent the first region.

109. The method of any of examples 106-108 wherein the target feature increases the absorption of energy at the first region relative to a second region adjacent the first region.

110. The method of any of examples 106-109 wherein the target feature is a recess extending at least partially into the actuation element, and wherein the applied energy penetrates the actuation element at the recess.

111. The method of any of examples 106-109 wherein the target feature is an absorptive coating.

112. The method of any of examples 106-109 wherein the target feature is an oxidized zone in the first region.

113. The method of any of examples 106-112 wherein the adjustable shunt is implanted in the eye of the patient to drain aqueous from an anterior chamber of the eye.

114. An implantable device for shunting fluid within a patient, the device comprising:
 a drainage element having a lumen extending therethrough;
 a flow control element moveable between at least a first position and a second position and configured to change a flow resistance through the device;
 an actuation element, wherein at least a portion of the actuation element is transitionable from a first material state to a second material state when heated above a transition temperature, and wherein the actuation element is configured to move the flow control element from the first position toward the second position when heated above the transition temperature; and
 a deflective element configured to direct energy received at the deflective element toward the actuation element to heat at least the portion of the actuation element above the transition temperature.

115. The device of example 108, further comprising a frame coupled to the drainage element, wherein the frame includes the deflective element.

116. The device of example 108 wherein the deflective element is positioned on the drainage element.

117. The device of any of examples 108-110 wherein the deflective element is configured to direct energy received in the form of visible and/or infrared electromagnetic radiation toward the actuation element to heat at least the portion of the actuation element.

118. The device of any of examples 108-111 wherein the deflective element is configured to direct energy received in the form of laser energy toward the actuation element to heat at least the portion of the actuation element.

119. The device of any of examples 108-112 wherein the deflective element is composed of a first material and the actuation element is composed of a second material, and wherein the first material is less absorptive than the second material.

120. The device of any of examples 114-119 wherein the deflective element includes a reflective element configured to reflect energy toward the actuation element.

121. The device of example 120 wherein the reflective element is at least partially composed of gold, palladium, and/or platinum.

122. The device of example 120 wherein the reflective element includes a mirror.

123. The device of any of examples 114-119 wherein the deflective element includes a refractive element configured to refract energy toward the actuation element.

124. The device of example 123 wherein the refractive element is at least partially composed of glass.

125. The device of example 123 wherein the refractive element includes a prism.

126. The device of any of examples 114-125 wherein the device includes a plurality of deflective elements.

127. The device of any of examples 114-126, wherein the actuation element includes a plurality of actuatable regions, and wherein the deflective element includes a plurality of deflective regions, with individual deflective regions of the deflective element corresponding to individual actuatable regions of the actuation element such that the individual actuation regions may be selectively actuated by selectively providing energy to the corresponding individual deflective regions.

128. The device of any of examples 114-127 wherein the first material state is a martensitic material state and the second material state is an austenitic material state.

129. The device of any of examples 114-128 wherein the actuation element is a first actuation element and wherein the deflective element is a first deflective element, the device further comprising:
  a second actuation element, wherein at least a portion of the second actuation element is transitionable from a third material state to a fourth material state when heated above a transition temperature of the second actuation element, and wherein the second actuation element is configured to move the flow control element from the second position toward the first position when heated above the second actuation element transition temperature; and
  a second deflective element configured to direct energy received at the second deflective element toward the second actuation element to heat the second actuation element above the second actuation element transition temperature.

130. The device of example 129 wherein the third material state is a martensitic material state and the fourth material state is an austenitic material state.

131. The device of any of examples 114-130 wherein the implantable device is a glaucoma shunt configured to drain aqueous from an anterior chamber of an eye of the patient.

132. An implantable device for shunting fluid within a patient, the device comprising:
  a fluid flow path configured to drain fluid from a first location in the patient having a first pressure to a second location in the patient having a second pressure less than the first pressure;
  a flow control element moveable between at least a first position and a second position and configured to change a flow resistance through the fluid flow path;
  an actuation element configured to move the flow control element from the first position toward the second position when actuated; and
  a deflective element configured to direct energy received at the deflective element toward the actuation element to actuate the actuation element.

133. The device of example 132, further comprising a frame coupled to the fluid flow path, wherein the frame includes the deflective element.

134. The device of example 132 wherein the deflective element is positioned on the fluid flow path.

135. The device of any of examples 132-134 wherein the deflective element is configured to direct energy received in the form of visible and/or infrared electromagnetic radiation toward the actuation element to actuate the actuation element.

136. The device of any of examples 132-135 wherein the deflective element is configured to direct energy received in the form of laser energy toward the actuation element to actuate the actuation element.

137. The device of any of examples 132-136 wherein the deflective element is composed of a first material and the actuation element is composed of a second material, and wherein the first material is less absorptive than the second material.

138. The device of any of examples 132-137 wherein the deflective element includes a reflective element configured to reflect energy toward the actuation element.

139. The device of example 138 wherein the reflective element is at least partially composed of gold, palladium, and/or platinum.

140. The device of example 138 wherein the reflective element includes a mirror.

141. The device of any of examples 132-137 wherein the deflective element includes a refractive element configured to refract energy toward the actuation element.

142. The device of example 141 wherein the refractive element is at least partially composed of glass.

143. The device of example 141 wherein the refractive element includes a prism.

144. The device of any of examples 132-143 wherein the device includes a plurality of deflective elements.

145. The device of any of examples 132-144 wherein the actuation element includes a plurality of actuatable regions, and wherein the deflective element includes a plurality of deflective regions, with individual deflective regions of the deflective element corresponding to individual actuatable regions of the actuation element such that the individual actuation regions may be selectively actuated by selectively providing energy to the corresponding individual deflective region.

146. The device of any of examples 132-145 wherein the actuation element is a first actuation element and wherein the deflective element is a first deflective element, the device further comprising:
  a second actuation element configured to move the flow control element from the second position toward the first position when actuated; and
  a second deflective element configured to direct energy received at the second deflective element toward the second actuation element to actuate the second actuation element.

147. The device of any of examples 132-146 wherein the implantable device is a glaucoma shunt configured to drain aqueous from an anterior chamber of an eye of the patient.

148. An implantable device for shunting fluid within a patient, the device comprising:

a drainage element having a lumen extending therethrough; and an actuation assembly configured to change a flow resistance through the device, wherein the actuation assembly includes— an actuation element, wherein at least a portion of the actuation element is transitionable from a first material state to a second material state when heated above a transition temperature; and a deflective element configured to direct energy received at the deflective element toward the actuation element to heat at least the portion of the actuation element above the transition temperature.

149. The device of example 148 wherein the deflective element is configured to direct energy received in the form of visible and/or infrared electromagnetic radiation toward the actuation element to heat at least the portion of the actuation element.

150. The device of example 148 wherein the deflective element is configured to direct energy received in the form of laser energy toward the actuation element to heat at least the portion of the actuation element.

151. The device of any of examples 148-150 wherein the deflective element is composed of a first material and the actuation element is composed of a second material, and wherein the first material is less absorptive than the second material.

152. The device of any of examples 148-151 wherein the deflective element includes a reflective element configured to reflect energy toward the actuation element.

153. The device of example 152 wherein the reflective element is at least partially composed of gold, palladium, and/or platinum.

154. The device of example 152 wherein the reflective element includes a mirror.

155. The device of any of examples 148-151 wherein the deflective element includes a refractive element configured to refract energy toward the actuation element.

156. The device of example 155 wherein the refractive element is at least partially composed of glass.

157. The device of example 155 wherein the refractive element includes a prism.

158. The device of any of examples 148-157 wherein the device includes a plurality of deflective elements.

159. The device of any of examples 148-158 wherein the actuation element includes a plurality of actuatable regions, and wherein the deflective element includes a plurality of deflective regions, with individual deflective regions of the deflective element corresponding to individual actuatable regions of the actuation element such that the individual actuation regions may be selectively actuated by selectively providing energy to the corresponding individual deflective region.

160. The device of any of examples 148-159 wherein the first material state is a martensitic material state and the second material state is an austenitic material state.

161. The device of any of examples 148-160 wherein the implantable device is a glaucoma shunt configured to drain aqueous from an anterior chamber of an eye of the patient.

162. A method of shunting fluid using an adjustable flow shunt implanted in a patient and having an actuation element, the method comprising:

indirectly applying energy to the actuation element, wherein indirectly applying energy to the actuation element comprises transmitting energy to a deflective element that redirects energy received at the deflective element towards the actuation element; and inducing, via the energy redirected to the actuation element, a geometry change in the actuation element, wherein the geometry change results in a change in flow resistance through the adjustable flow shunt.

163. The method of example 162 wherein transmitting energy to the deflective element comprises transmitting energy to the deflective element using an energy source positioned external to the patient.

164. The method of example 162 or 163 wherein the deflective element is implanted in the patient.

165. The method of example 164 wherein the deflective element is coupled to the shunt.

166. The method of any of examples 162-165 wherein the energy is visible and/or infrared electromagnetic radiation.

167. The method of any of examples 162-166 wherein the energy is laser energy.

168. The method of any of examples 162-167 wherein the deflective element is composed of a first material and the actuation element is composed of a second material, and wherein the first material is less absorptive than the second material.

169. The method of any of examples 162-168 wherein the deflective element includes a reflective element that reflects received energy toward the actuation element.

170. The method of example 169 wherein the reflective element is at least partially composed of gold, palladium, and/or platinum.

171. The method of example 169 wherein the reflective element includes a mirror.

172. The method of any of examples 162-168 wherein the deflective element includes a refractive element that refracts energy toward the actuation element.

173. The method of example 172 wherein the refractive element is at least partially composed of glass.

174. The method of example 172 wherein the refractive element includes a prism.

175. The method of any of examples 162-174 wherein the adjustable shunt is implanted in the eye of the patient to drain aqueous from an anterior chamber of the eye.

176. A method of manufacturing an adjustable shunt having a shunting element, a flow control element, and a shape memory actuation element, the method comprising:

depositing a first material and/or a second material on a substrate, wherein the first material is deposited in a pattern corresponding to the shunting element and the flow control element, and wherein the second material is deposited in a pattern corresponding to one or more void spaces of the adjustable shunt;

removing the deposited second material, wherein removing the deposited second material (i) creates a lumen extending through the shunting element and (ii) enables the flow control element to move relative to the shunting element; and securing the shape memory actuation element to the flow control element and/or the shunting element, wherein, once the shape memory actuation element is secured to the flow control element, the shape memory actuation element is configured to selectively drive movement of the flow control element relative to the shunting element.

177. The method of example 176 wherein depositing the first material and the second material comprises depositing the first material and the second material via a vapor deposition process.

178. The method of example 176 or 177 wherein depositing the first material and the second material comprises depositing the first material and second material in individual layers of about 5 micron or less.

179. The method of any of examples 176-178 wherein removing the second material comprises etching away the second material.

180. The method of any of examples 176-179 wherein the first material is a polymer and/or metal.

181. The method of any of examples 176-180 wherein the first material is palladium, rhodium, and/or a nickel-cobalt alloy.

182. The method of any of examples 176-181 wherein the second material is copper.

183. The method of any of examples 176-182 wherein the shape memory actuation element is composed of nitinol.

184. A method of manufacturing an adjustable shunt having a shape memory actuation element, the method comprising:
depositing a first material and/or a second material on a substrate, wherein the first material is deposited in a pattern corresponding to a first component and a second component of the adjustable shunt, and wherein the second material is deposited in a pattern corresponding to one or more void spaces of the adjustable shunt;
removing the deposited second material, wherein, after the deposited second material is removed, the first component is at least partially constrained within and moveable relative to the second component without requiring assembly of the first component and the second component; and
securing the shape memory actuation element to the first component and/or the second component,
wherein, once secured to the first component and/or the second component, the shape memory actuation element is configured to selectively drive movement of the first component relative to the second component.

185. The method of example 184 wherein depositing the first material and the second material comprises depositing the first material and the second material via a vapor deposition process.

186. The method of example 184 or 185 wherein depositing the first material and the second material comprises depositing the first material and second material in individual layers of about 5 micron or less.

187. The method of any of examples 184-186 wherein removing the second material comprises etching away the second material.

188. The method of any of examples 184-187 wherein the first material is a polymer and/or metal.

189. The method of any of examples 184-188 wherein the first material is palladium, rhodium, and/or a nickel-cobalt alloy.

190. The method of any of examples 184-189 wherein the second material is copper.

191. The method of any of examples 184-190 wherein the first component is a flow control element and the second component is a shunting element.

192. The method of any of examples 184-191 wherein the shape memory actuation element is composed of nitinol.

193. A method of manufacturing an adjustable shunt, the method comprising:
forming, via a layered deposition process, a shunting element and a flow control element in an assembled configuration in which the flow control element is moveable relative to the shunting element; and
securing an actuation element to the shunting element and/or the flow control element, wherein, once secured to the shunting element and/or the flow control element, the actuation element is configured to selectively move the flow control element relative to the shunting element.

194. The method of example 193 wherein forming the shunting element and the flow control element comprises simultaneously forming the shunting element and the flow control element.

195. The method of example 193 or 194 wherein forming the shunting element and the flow control element comprises:
depositing a first material and a second material in layers of about 5 micron or less; and
etching away the second material to form the shunting element and the flow control element.

196. The method of any of examples 193-195 wherein the layered deposition process is a vapor deposition process or a chemical deposition process.

197. The method of any of examples 193-196 wherein the actuation element is composed of nitinol.

198. A method of manufacturing an adjustable shunt having a shunting element and a flow control element, the method comprising:
forming, via a photolithographic process, the shunting element and the flow control element in an assembled configuration in which the flow control element is moveable relative to the shunting element; and
securing an actuation element to the shunting element and/or the flow control element,
wherein, once secured to the shunting element and/or the flow control element, the actuation element is configured to selectively move the flow control element relative to the shunting element.

199. The method of example 198 wherein the actuation element is composed of nitinol.

CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, any of the features of the intraocular shunts described herein may be combined with any of the features of the other intraocular shunts described herein and vice versa. Moreover, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions associated with intraocular shunts have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An implantable medical device for draining fluid from a first body region to a second body region, the device comprising:
   a drainage element having a lumen extending therethrough and configured to fluidly connect the first body region and the second body region;
   a flow control element selectively moveable through at least three discrete positions, wherein each discrete position is associated with a corresponding fluid resistance through the device and
   an actuation assembly configured to incrementally move the flow control element through at least one of the at least discrete positions during actuation of the actuation assembly.

2. The device of claim 1 wherein the actuation assembly includes a ratchet mechanism configured to move the flow control element through the plurality of discrete positions.

3. The device of claim 2 wherein the ratchet mechanism includes at least three teeth.

4. The device of claim 3 wherein the plurality of teeth correspond to the at least three discrete positions.

5. The device of claim 1 wherein the actuation assembly includes at least one actuation element and a ratchet mechanism.

6. The device of claim 5 wherein the implantable medical device is a glaucoma shunt, and wherein the first body region is an anterior chamber of an eye.

7. The device of claim 1 wherein the flow control element is configured to change a diameter of the lumen as it moves between the at least three discrete positions.

8. The device of claim 1 wherein the flow control element is selectively moveable through at least four discrete positions, and wherein each of the at least four discrete positions is associated with a unique fluid resistance through the device.

9. The device of claim 1 wherein the actuation assembly includes a shape memory actuation element.

10. The device of claim 1 wherein the actuation assembly is further configured to retain the flow control element at a particular discrete position of the at least three discrete positions following actuation of the actuation assembly.

11. An implantable medical device for draining fluid from a first body region to a second body region, the device comprising:
    a drainage element having a lumen extending therethrough and configured to fluidly connect the first body region and the second body region;
    a flow control element moveable through at least three discrete positions; and
    an actuator, wherein, in response to being actuated, the actuator moves the flow control element from its current discrete position of the at least three discrete positions to a different discrete position of the at least three discrete positions.

12. The device of claim 11 wherein the flow control element is moveable through at least four discrete positions.

13. The device of claim 11 wherein the flow control element is moveable through at least five discrete positions.

14. The device of claim 11 wherein at least some of the at least three discrete positions provide a unique relative fluid resistance through the device.

15. The device of claim 11 wherein each of the at least three discrete positions provides a different fluid resistance through the device.

16. The device of claim 11, further comprising a ratchet, wherein the ratchet is configured to retain the flow control element at the different discrete position after the actuator is actuated to move the flow control element to the different discrete position.

17. The device of claim 11 wherein the actuator includes a shape memory actuation element.

18. The device of claim 11 wherein the device is an intraocular shunting device.

* * * * *